United States Patent
Chiesa et al.

(12) 
(10) Patent No.: US 6,787,310 B2
(45) Date of Patent: Sep. 7, 2004

(54) STRAND DISPLACEMENT METHODS EMPLOYING COMPETITOR OLIGONUCLEOTIDES FOR ISOLATING ONE STRAND OF A DOUBLE-STRANDED NUCLEIC ACID

(75) Inventors: Claudia Chiesa, Redwood City, CA (US); Gary P. Schroth, San Ramon, CA (US); Michael Egholm, Woodbridge, CT (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/909,001

(22) Filed: Jul. 18, 2001

(65) Prior Publication Data

US 2003/0148277 A1 Aug. 7, 2003

Related U.S. Application Data

(60) Provisional application No. 60/222,686, filed on Aug. 2, 2000.

(51) Int. Cl.[7] ............................. C12Q 1/68; C07H 21/04
(52) U.S. Cl. ............................ 435/6; 436/94; 536/25.4
(58) Field of Search ............................... 435/6; 436/94; 536/25.4

(56) References Cited

FOREIGN PATENT DOCUMENTS

WO    WO 99 07890    2/1999

OTHER PUBLICATIONS

Peffer, "Strand–Invasion of Duplex DNA by Peptide Nucleix Acid Oligomers", Proceedings of the National Academy of Sciences of the USA, National Academy of Science, Washington, U.S., Nov. 15, 1993, pp. 10648–10652, vol. 90.

PCT International Search Report, International Application No. PCT/US 01/22782.

*Primary Examiner*—Kenneth R. Horlick
(74) *Attorney, Agent, or Firm*—Scott R. Bortner; Andrew K. Finn

(57) ABSTRACT

The present invention provides methods and kits for isolating one strand of a double-stranded target nucleic acid. The method capitalizes on the differences in the kinetics and thermodynamic stabilities between conventional DNA/DNA, DNA/RNA and RNA/RNA duplexes and heteroduplexes in which one strand of the heteroduplexe is a nucleobase polymer having a net positively charged or net neutral backbone, such as a PNA.

25 Claims, 9 Drawing Sheets

SEQUENCE LISTING

```
<160> NUMBER OF SEQ ID NOS: 2

<210> SEQ ID NO 1
<211> LENGTH: 10
<212> TYPE: DNA
<213> ORGANISM: Unknown
<220> FEATURE:
<223> OTHER INFORMATION: synthetic DNA

<400> SEQUENCE: 1
gaatcgcgat                                                          10

<210> SEQ ID NO 2
<211> LENGTH: 10
<212> TYPE: DNA
<213> ORGANISM: Unknown
<220> FEATURE:
<223> OTHER INFORMATION: synthetic DNA

<400> SEQUENCE: 2
cttagcgcta                                                          10
```

STRAND DISPLACEMENT METHODS EMPLOYING COMPETITOR OLIGONUCLEOTIDES FOR ISOLATING ONE STRAND OF A DOUBLE-STRANDED NUCLEIC ACID

1. FIELD OF THE INVENTION

The present invention relates to compositions and methods for isolating one strand of double-stranded nucleic acids.

2. BACKGROUND

Many techniques in the field of molecular biology involve hybridizing a target nucleic acid to a support-bound or solution-phase single-stranded oligonucleotide probe for analyzing, capturing, isolating and/or detecting the target nucleic acid. Such techniques range from Sanger-type DNA sequencing (see, e.g., Sanger et al., 1977, Proc. Natl. Acad. Sci. USA 74:5463–5467; Ansorge et al., 1987, Nucl. Acids Res. 15:4593–4602; Smith et al., 1985, Nucl. Acids Res. 13:2399–2412; Smith, et al., 1986, Nature 321:674–679; Prober et al., 1987, Science 238:336–341), where a labeled or unlabeled primer is annealed to one strand of a target and enzymatically extended in the presence of 2',3'-dideoxyribonucleotide terminators (see also, Carrilho, 2000, Electrophoresis 21:55–65 and Kheterpal & Mathies, 1999, Anal. Chem. 71:31A—37A) to array-based gene expression, genotyping, gene mapping and nucleic acid sequencing assays (see, e.g., U.S. Pat. Nos. 5,202,231, 5,695,940 and 5,525,464, WO 95/09248, Khrapko et al., 1991, DNA Sequence 1:375–388; Southern et al., 1992, Genomics 13:1008–1017; Pease et al., 1994, Proc. Natl. Acad. Sci. USA 91:5022–5026; for reviews of the various array-based assays commonly employed in the art see Thompson & Furtado, 1999, Analyst 124:1133–1136; Rockett & Dix, 2000, Xenobiotica 30:155–177; Granjeaud et al., 1999, Bioessays 21:781–790; Lipscutz et al., 1999, Nat. Genet. 21(1 Suppl.):20–24; DeRisi & Iyer, 1999, Curr. Opin. Oncol. 11:76–79; Blanchard, 1998, Genet. Eng. 20:111–123; Case-Green et al., 1998, Curr. Opin. Chem. Biol. 2:404–410; Johnston, 1998, Curr. Biol. 8:R171-174; de Saizieu et al., 1998, Nat. Biotechnol. 16:45–48; and Marshall & Hodgson, 1998, Nat. Biotechnol. 16:27–31).

When the target nucleic acid is single-stranded, hybridization to the oligonucleotide probe occurs relatively easily. But when the target nucleic acid is double-stranded, reassociation of the two target strands strongly competes with, and usually out-competes, hybridization between the target and oligonucleotide probe, especially under the high-salt stringent conditions commonly employed in these assays.

Unfortunately, target nucleic acids are rarely available in single-stranded form. Indeed, most target nucleic acids are double-stranded. For example, genomic DNA, genomic fragments and cDNA are double-stranded. Moreover, one of the most commonly-used amplification techniques for generating analyzable quantities of a specific nucleic acid of interest, the polymerase chain reaction ("PCR" see, e.g., U.S. Pat. No. 4,683,202; Sambrook et al., 2d ed. 1989, MOLECULAR CLONING: A LABORATORY MANUAL, Cold Springs Harbor, N.Y.) generates double-stranded amplicons, or target nucleic acids.

Current methods for generating single-stranded target nucleic acids include exonuclease digestion of one strand of the double-stranded target (see, e.g., Hannon et al., 1993, Anal. Biochem. 212:421–427), asymmetric PCR amplification (see, e.g., Stürzl and Roth, 1990, Anal. Biochem. 185:164–169), generating single-stranded RNA targets by in vitro transcription of double-stranded PCR amplicons having a T7 or T3 RNA polymerase promoter (see, e.g., Yang and Melera, 1992, BioTechniques 13:922–927) and cloning with Ml 3 (see, e.g., Sambrook, et al., supra). Each of these methods has significant drawbacks that either limit its general applicability and/or significantly increase the time and expense of the assay.

Accordingly, there remains a need in the art for simple methods of generating and isolating one strand of a double-stranded target nucleic acid for assays involving hybridization with a single-stranded oligonucleotide probe, such as Sanger-type sequencing reactions, and array-based mapping, genotyping, expression and sequencing applications.

3. SUMMARY OF THE INVENTION

In one aspect, the present invention provides a method for capturing or isolating one strand of a double-stranded target nucleic acid. The method is based, in part, on the observations that the thermodynamic stabilities and/or kinetics of formation of nucleic acid duplexes under varying conditions of ionic strength depend upon the nature of the internucleoside linkages comprising the strands of the duplex. For example, as evidenced by the occurrence of double-stranded DNAs in nature and the ability of DNAs and RNAs to form homo and hybrid duplexes under physiological conditions, duplexes formed between single-stranded nucleic acids having like-charged internucleoside linkages, such as DNAs and RNAs which have negatively charged sugar phosphodiester interlinkages, are relatively stable under conditions of physiological ionic strength (approximately 100 mM NaCl), temperature (approximately 37° C.) and pH (approximately pH 7.2). However, under conditions of low ionic strength (approximately 10 mM NaCl or lower), such DNA/DNA, RNA/RNA and DNA/RNA duplexes tend to dissociate (see, e.g., Egholm et al., 1993, Nature 365:566–568). While not intending to be bound by any particular theory, it is believed that the observed dissociation at conditions of low ionic strength is due to interstrand electrostatic repulsion caused by the negatively charged sugar phosphodiester nucleobase interlinkages.

On the contrary, heteroduplexes in which one strand of the duplex is a conventional DNA or RNA and the other strand is a nucleic acid analog that has a net uncharged or net positively charged backbone (e.g., a PNA) are quite stable at conditions of low ionic strength (see, e.g., id.). In fact, at NaCl concentrations between about 0 and 10 mM, and even as high as 500 mM, such heteroduplexes are significantly more stable than their corresponding DNA/DNA, RNA/RNA or DNA/RNA duplexes (id).

Moreover, the formation of these heteroduplexes is favored kinetically over the formation of the corresponding DNA/DNA, DNA/RNA and RNA/RNA duplexes under the same conditions of low ionic strength. These observed differences in kinetics are independent of the length of the heteroduplex. For example, while a relatively long DNA/DNA target duplex (e.g., $\geq 100$ bp) is typically more thermodynamically stable than a short PNA/DNA heteroduplex (e.g., $\leq 20$ bp) at virtually any ionic strength, if the DNA/DNA target duplex is dissociated and contacted with even a short complementary PNA under conditions of low ionic strength (e.g., less than 10 mM NaCl), the formation of the PNA/DNA heteroduplex will be kinetically favored over the reannealing or reassociation of the DNA target strands. Only as the system is brought to equilibrium will the PNA be displaced by the complementary DNA target strand.

The methods of the invention capitalize on these observed kinetic and thermodynamic stability differences to easily and efficiently isolate one strand of a double-stranded target nucleic acid. Generally, the method involves contacting a double-stranded target nucleic acid with a single-stranded competitor oligonucleotide ("competitor oligo") that is capable of hybridizing to one strand of the double-stranded target. The competitor oligo is a nucleic acid analog which comprises a combination of negatively charged (e.g., a native sugar phosphodiester), positively charged (e.g., a sugar glycosyl or positive amide) and/or uncharged (e.g., neutral amide or morpholino-phosphoramidate) nucleobase interlinkages such that the competitor oligo has a net positive charge or a net neutral charge at the desired pH and temperature of use (typically pH 6–9 and 20–40° C.). Preferably, the competitor oligo is wholly composed of uncharged nucleobase interlinkages, and optionally includes 3–4 positive interlinkages. The nucleobase sequence of the competitor oligo is at least partially complementary to a portion of one strand of the double-stranded target such that it can hybridize to its complementary target strand.

The target nucleic acid is contacted with the competitor oligo under conditions in which the target strands tend to dissociate from one another and the competitor oligo hybridizes with its complementary target strand, forming a target-strand:competitor oligo heteroduplex and a dissociated target strand. The desired strand of the double-stranded target may then be conveniently recovered by isolating either the dissociated target strand or the heteroduplex using standard isolation and/or capture techniques.

Whether the system is permitted to reach equilibrium prior to isolating the heteroduplex and/or dissociated strand will typically depend upon the thermodynamic stabilities of the double-stranded target and the target-strand:competitor oligo heteroduplex under the condition of the assay, which in turn will depend upon the relative lengths (in nucleobases) of the respective target duplex and heteroduplex. Generally, if the thermodynamic stability (as indicated by thermal melting temperature or $T_m$) of the target duplex is significantly greater than the thermodynamic stability of the heteroduplex, the system should not be permitted to reach equilibrium. If the thermodynamic stabilities are reversed, or if they are approximately equal, the system may be permitted to reach equilibrium. For example, if the competitor oligo is of a length (in nucleobase units) that is approximately equal to the length of the target nucleic acid, the system may be permitted to reach equilibrium prior to isolating the desired target strand, as the heteroduplex will typically be more thermodynamically stable than the reassociated or reannealed target. However, in instances where the reassociated or reannealed target is thermodynamically more stable than the heteroduplex (such as when the competitor oligo is significantly shorter than the target), the desired strand of the target nucleic acid should be isolated before the system reaches equilibrium.

The method of isolating one strand of a double-stranded target nucleic acid may be carried out in a variety of alternative modes. In one embodiment, the double-stranded target is contacted with the competitor oligo under conditions in which the double-stranded target is stable (i.e., the strands of the target do not readily dissociate). Following contact, the conditions of the mixture are then altered so as to promote dissociation of the target strands and hybridization between the competitor oligo and its complementary target strand.

The conditions may be altered in a single step, or alternatively they may be altered in two or more steps. If a single step is used, the new conditions should simultaneously favor target strand dissociation and target-strand:competitor oligo heteroduplex formation. If a two-step process is used, the conditions are first altered so as to promote target strand dissociation and thereafter altered again so as to promote target-strand:competitor oligo heteroduplex formation.

The conditions may also be cycled. For example, following contact, the temperature of the sample may be cycled between two or more different temperatures. In one convenient embodiment, following contact, the temperature of the sample may be increased to a temperature that is above the thermal melting temperature ($T_m$) of the double-stranded target and below the $T_m$ of the heteroduplex. The temperature of the sample may then be cycled between this temperature and a second temperature that is above the $T_m$ of the heteroduplex. By choosing a cycling time that takes advantage of the faster kinetics of heteroduplex formation, temperature cycling may be used to drive the dissociation of the double-stranded target and efficient formation of the heteroduplex.

In another embodiment, the strands of the double-stranded target nucleic acid are dissociated prior to contact with the competitor oligo. The conditions used to dissociate the double-stranded target ("denaturing conditions") may simultaneously favor target dissociation and target-strand:competitor oligo heteroduplex formation, thereby eliminating the need for further alteration of the conditions. Alternatively, denaturing conditions that do not favor or promote target-strand:competitor oligo heteroduplex formation may be used, and the conditions altered after contact to promote heteroduplex formation. Temperature cycling may be used to drive efficient heteroduplex formation, as previously described.

Regardless of the method used to dissociate the double-stranded target and form the and target-strand:competitor oligo heteroduplex, the dissociated target strand and heteroduplex may be separated from one another and the desired target strand recovered for subsequent use.

The dissociated target strand and target-strand:competitor oligo hetereoduplex may be separated from one another using virtually any technique. For example, the dissociated strand and heteroduplex may be separated by gel electrophoresis, one or both of the respective bands excised from the gel and the nucleic acids eluted from the excised bands. Alternatively, the dissociated target strand and the heteroduplex may be separated from one another by capture. When separated by capture, either the desired target strand or undesired target strand may be captured. If the desired target strand is captured, it may be dissociated and recovered for subsequent use. Capturing the undesired target strand leaves behind the desired target strand, which can be recovered for subsequent use either with or without further purification.

In one embodiment, the dissociated target strand may be hybridized to a complementary oligonucleotide capture probe that includes a capture moiety, such as a biotin, a solid support or a capture sequence, and the hybridized complex isolated by means of the capture moiety. Preferably, the complementary capture probe also comprises nucleobase interlinkages having a net positive or net neutral charge so that the dissociated target strand can be captured under conditions that do not promote reassociation or reannealing of the target strands. Following capture, the complex can be dissociated and the target strand isolated therefrom.

Alternatively, the target-strand:competitor oligo heteroduplex may be isolated by capture. In one convenient embodiment, the competitor oligo includes a capture moiety, such as a biotin, a capture sequence or a solid support, and the heteroduplex is isolated from the dissociated target strand by means of the capture moiety. For example, if the competitor oligo includes a biotin capture moiety, the heteroduplex may be isolated from the dissociated target strand by contacting the sample with immobilized streptavidin, for example by passing the sample through a column packed with streptavidin-coated beads or by contacting the sample with straptavidin-coated magnetic beads, which can be removed with the aid of a magnet. If the competitor oligo includes a capture sequence, the heteroduplex may be isolated from the dissociated target strand via a complementary capture probe that also includes a capture moiety, such as a biotin or a solid support. The capture probe may be an RNA or a DNA oligomer or, like the competitor oligo, it may comprise a backbone having a net positive or net neutral charge at the pH and temperature of the assay. When the competitor oligo includes a solid support capture moiety, the heteroduplex may be isolated from the dissociated target strand by, e.g., filtration, decanting, etc. If the solid support is magnetic, the heteroduplex may be conveniently isolated with the aid of a magnet.

In another embodiment, the heteroduplex is isolated by capture with a capture probe capable of forming a triplex with the heteroduplex. Preferably, the triplex capture probe is modified to include a capture moiety, such as biotin or a solid support, as previously described. In one convenient embodiment, the triplex-forming capture probe is a PNA (see, e.g., U.S. Pat. Nos. 5,986,053; 5,641,625; and 5,539,082, which are incorporated herein by reference).

In another aspect, the invention provides kits for practicing the methods of the invention. Generally, the kits comprise a competitor oligo complementary to at least a portion of one strand of a target nucleic acid of interest and buffers useful for dissociating the double-stranded target and effecting formation of a target-strand:competitor oligo heteroduplex. The kit may also comprise capture probes or other means for isolating either the dissociated target strand or heteroduplex, or both. The competitor oligo may be optionally modified with a capture moiety to facilitate capture of the target-strand:competitor oligo heteroduplex, as previously described. Alternatively, the kit may further comprise reagents useful for modifying the competitor oligo, a capture probe or both, with a capture moiety.

Target strands isolated according to the methods and kits of the invention may be further manipulated using techniques well known in the art. For example, the isolated strand may be used as a template in a subsequent PCR amplification, as a target for solution-phase and/or array-based sequencing by hybridization, mapping, gene expression and genotyping assays, or as a template in a Sanger-type sequencing reaction.

4. BRIEF DESCRIPTION OF THE FIGURES

FIG. 1 provides an illustration of the general method of the invention;

5. DETAILED DESCRIPTION OF THE INVENTION

Figure 1:
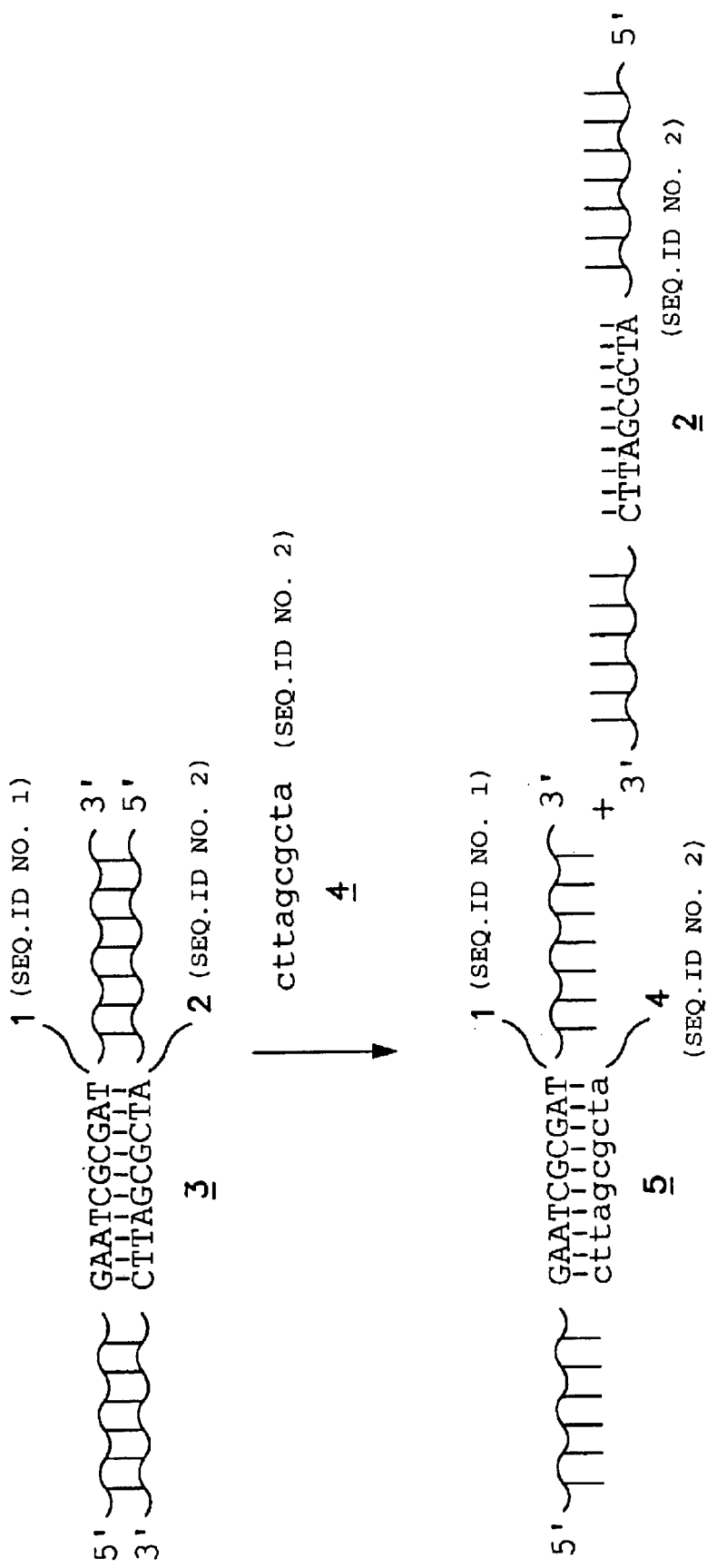

The present invention provides a rapid, efficient, and specific method of isolating one strand of a double-stranded target nucleic acid. By utilizing competitor oligonucleotides in which the nucleobases are connected to a backbone having a net positive or net neutral charge at the pH and temperature of the assay, the invention capitalizes on the observed advantageous kinetic and/or thermodynamic properties of nucleic acid heteroduplexes compared with conventional DNA/DNA, DNA/RNA and RNA/DNA duplexes to provide methods for isolating one strand of a double-stranded target nucleic acid that provide significant advantages over presently available methods.

As will be discussed in more detail below, single-stranded nucleobase polymers having positively charged and/or uncharged nucleobase interlinkages are known in the art. One type of uncharged nucleobase polymer, commonly referred to in the art as a "polyamide nucleic acid" or "PNA," comprises a series of nucleobases linked to a neutral polyamide backbone. The kinetics of formation and thermodynamic stabilities of heteroduplex nucleic acids in which one strand is an uncharged nucleobase polymer, such as a PNA, are quite distinct from the corresponding duplexes in which both strands have native sugar phosphodiester (i.e., negatively charged) nucleobase interlinkages, such as DNA/DNA, RNA/RNA and DNA/RNA duplexes. Quite significantly, PNA/DNA and PNA/RNA heteroduplexes are significantly more thermostable than their corresponding DNA/DNA, RNA/RNA and DNA/RNA duplexes over a wide range of buffer conditions (Egholm et al., 1993, Nature 365:566–568). Moreover, the formation of the PNA/DNA and PNA/RNA heteroduplexes is kinetically favored over the same range of buffer conditions. Under conditions of low ionic strength (e.g., $\leq 10$ mM NaCl), the favorable kinetics of formation is independent of thermodynamic stability (as measured by $T_m$). For example, in some instances, the target nucleic acid duplex will be more thermo-stable than a particular heteroduplex at virtually every ionic strength (e.g., a long 100 bp target duplex vs. a short, 20 bp heteroduplex). Even in this instance, under conditions of low ionic strength, the formation of the heteroduplex is kinetically favored over the formation of more thermostable duplex. Thus, if a 100 bp dissociated target is contacted with a 20 nucleobase complementary PNA under conditions of low ionic strength, PNA/DNA heteroduplex formation will be favored kinetically over reannealing or reassociation of the target strands.

While not intending to be bound by any particular theory of operation, as the PNA backbone is uncharged, it is believed that the observed favorable kinetic and/or thermostability properties of PNA/DNA and PNA/RNA heteroduplexes discussed above are due, in part, to the absence of phosphodiester electrostatic repulsions between the two strands of the heteroduplex. This theory is supported by experiments showing that PNA/DNA heteroduplexes and the corresponding DNA/DNA duplexes have approximately equal thermostabilities at ionic strengths above 1 M NaCl (Egholm et al., 1993, supra).

The observed kinetic and/or thermostability differences between heteroduplexes and their corresponding duplexes are most pronounced at conditions of extremely low to low ionic strength. For example, at 10 mM NaCl, the thermal melting temperature ($T_m$) of a PNA/DNA heteroduplex dodecamer was found to be over 30° C. higher than the $T_m$ of the corresponding DNA/DNA duplex. However, these differences are observed even at moderate ionic strengths. For example, even at 100 mM NaCl, the PNA/DNA heteroduplex dodecamer had a significantly higher (approx. 20° C.) $T_m$ than the corresponding DNA/DNA duplex (Egholm et al., 1993, supra).

PNAs also have the ability to invade double-stranded DNAs comprising a complementary sequence of nucleobases (see, e.g., Nielson et al., 1992, Nucl. Acids Res. 21:197–200; Peffer et al., 1993, Proc. Natl. Acad. Sci. USA 90:10648–10652; Cherny et al., 1993, Proc. Natl. Acad. Sci. USA 90:1667–1670). The PNA hybridizes to the complementary strand via Watson-Crick base pairing, while the other strand is displaced. If the double-stranded DNA is substantially longer than the complementary portion of the PNA, then the displaced strand can form a D-loop (see id.). Thus, even at physiological conditions where a double-stranded target is stable, PNAs tend to hybridize to their complementary strand.

As will be discussed in more detail below, the Applicants have discovered that the tendency of PNAs to invade complementary double-stranded nucleic acids and the observed kinetic and/or thermostability differences between DNA/DNA, DNA/RNA and RNA/RNA duplexes and PNA/DNA and PNA/RNA heteroduplexes can be exploited to efficiently, rapidly and easily isolate one strand of a double-stranded target nucleic acid.

The ability of PNAs to form stable duplexes with single-stranded DNA and RNA, or stable triplexes with DNA, has been exploited in a number of applications for the purification of single-stranded or double-stranded nucleic acids. For example, a PNA linked to a polyhistidine tail has been used to purify single-stranded messenger RNA on a nickel column (see Ørum et al., 1995, BioTechniques 19:472–480). In this method, single-stranded mRNA transcribed in vitro was contacted with a PNA-polyhistidine conjugate in a buffer containing 2 M urea, 20 mM $Na_2HPO_4$ (pH 8.0), 500 mM NaCl, 0.1% TRITON X-100® and the mRNA-PNA-polyhistidine complex was captured by passing the sample across a nickel column.

Double-stranded human genomic DNA has been purified from biological samples using biotin-labeled PNA (see Seeger et al., 1997, BioTechniques 23:512–517; Boffa et al, 1995, Proc. Natl. Acad. Sci. USA 92:1901–1905). For example, transcriptionally active double-stranded genomic DNA fragments have been isolated by invasion and hybridization of a PNA comprising the nucleobase sequence $(CTG)_7$ to form D-loops (see Boffa et al., supra). In another example, double-stranded genomic DNA was isolated from human blood by hybridization with a biotin-labeled PNA comprising the sequence $T_7$ (see Seeger et al., supra). The labeled PNA formed high-affinity triplexes with $A_7$ sequences in the double-stranded genomic DNA. In both examples, the biotin label on the PNA was used to capture the D-loops or the triplex hybrids on streptavidin-coated magnetic beads.

Techniques for detecting single-base mutations using PNA-nucleic acid hybridization also have been described (see Igloi, 1999, BioTechniques 27:798–808; Igloi, 1998, Proc. Natl. Acad. Sci. USA 95:8562–8567). For example, a PNA complementary to a single-stranded DNA oligonucleotide was added to native polyacrylamide gel solution prior to polymerization. When the complementary single-stranded DNA oligonucleotide was run on the gel, it hybridized to the PNA molecules immobilized in the gel matrix (which do not migrate, as they are uncharged). The migration of the DNA/PNA hybrid was retarded relative to the migration of unhybridized, uncomplementary control DNA oligonucleotides. A collection of other single-stranded DNA oligonucleotides was also run on the gels. Each of these oligonucleotides contained a single base mismatch with the PNA. By adjusting the running temperature of the gel, the PNA could be caused to hybridize to (and therefore retard the migration of) only the perfectly complementary oligonucleotide. The migration of mismatched oligonucleotides was not retarded, thus allowing for the detection of single-base pair mismtaches.

PNAs have further been used to inhibit the amplification of nucleic acids in PCR reactions (see, e.g., U.S. Pat. No. 5,972,610). In this method, a PNA complementary to a nucleic acid in the sample whose amplification is not desired is hybridized to that nucleic acid, thereby effectively blocking its amplification.

Lastly, labeled PNAs have been used in lieu of standard Southern hybridization blots to detect target nucleic acids (see Perry-O'Keefe et al., 1996, Proc. Natl. Acad. Sci. USA 93:14670–14675). In this method, labeled PNA was added to denatured target DNA. The mixture was loaded directly onto an electrophoresis system for size separation. The PNA/DNA hybrids remained associated during electrophoresis. After electrophoresis and blotting onto a membrane, the labeled hybrids were detected using standard chemiluminescent techniques without the need for hybridizing a labeled oligonucleotide to the membrane-bound target DNA.

However, unlike the present invention, none of the above-described techniques exploits differences between the kinetics and/or thermodynamic stabilities of PNA/DNA (or PNA/RNA) heteroduplexes and DNA/DNA (or DNA/RNA or RNA/RNA) duplexes to isolate one strand of a double-stranded target nucleic acid.

5.1 Abbreviations and Conventions

The abbreviations used throughout the specification and in the FIGS. to refer to target nucleic acids and competitor oligos comprising specific nucleobase sequences are the conventional one-letter abbreviations. Capital letters represent target nucleic sequences (e.g., RNA and DNA sequences) and lower case letters represent competitor oligo sequences (e.g., PNA sequences). Thus, when included in a target nucleic acid, the naturally occurring encoding nucleobases are abbreviated as follows: adenine (A), guanine (G), cytosine (C), thymine (T) and uracil (U). When included in a competitor oligo sequence, the naturally occuring encoding nucleobases are abbreviated as follows: adenine (a), guanine (g), cytosine (c), thymine (t) and uracil (u).

Also, unless specified otherwise, target nucleic acid sequences that are represented as a series of one-letter abbreviations are presented in the 5'->3' direction. Competitor oligo sequences that have 5' and 3' termini are also presented in the 5'->3' direction. Competitor oligo sequences that have amino and carboxy termini, such as PNAs, are presented in the carboxy-to-amino direction.

5.2 The Invention

The general method for isolating one strand of a double-stranded target nucleic acid according to the invention is illustrated in FIG. 1. Referring to FIG. 1, a double-stranded target nucleic acid of interest 3 is contacted with a competitor oligonucleotide (competitor oligo) 4. The double-stranded target 3 comprises a first strand 1 and a second strand 2, and the competitor oligo 4 is complementary to at least a portion of the first strand 1. In FIG. 1, the complementary region is shown as an internal sequence of the target nucleic acid, although as will be illustrated later, the complementary region could be at one or both termini. The target 3 and competitor oligo 4 are contacted under conditions that favor dissociation of the doubled-stranded target 3 into first strand 1 and second strand 2 and hybridization between competitor oligo 4 and first strand 1, thereby yielding dissociated second strand 2 and first strand:competitor oligo heteroduplex 5. The conditions under which target 3 and competitor oligo 4 are contacted may simultaneously favor target strand 3 dissociation and heteroduplex 5 formation, or may be altered in steps to achieve first and second strand dissociation and heteroduplex 5 formation, as will be discussed in more detail, below. The target 3 may be contacted with competitor oligo 4 prior to, concomitant with, or after dissociating double-stranded target 3 into first and second strands 1 and 2, respectively.

In FIG. 1 and throughout the specification, the expressions "first strand" and "second strand" are used to refer to specific strands of the double-stranded target nucleic acid. It will be understood that these expressions are completely arbitrary and are used merely as a convenient means of identifying and/or discussing the individual target strands. No structural, functional, informational or other characteristic properties are intended to be implied by these expressions. For example, where the double-stranded target nucleic acid is a gene or portion of a gene, the "first strand" may be either the coding strand or the non-coding strand. Thus, the expressions "first strand" and "second strand" merely facilitate distinguishing the two strands of the double-stranded target from one another, and are used solely as an aid in describing the invention and are not intended to limit the scope of the invention in any way.

Moreover, the specification makes reference to a variety of different types of nucleic acid duplexes. As used herein, the expression "heteroduplex" refers to double-stranded nucleic acids in which at least one strand is a competitor oligo, as that expression is defined herein. For example, duplexes formed between a DNA or RNA strand and a PNA strand (PNA/DNA and PNA/RNA, respectively) are referred to herein as "heteroduplexes." All other double-stranded nucleic acids, including DNA/DNAs, RNA/RNAs and DNA/RNAs, are referred to as "duplexes." Duplexes in which both strands are DNA or both strands are RNA are referred to as "homoduplexes." Duplexes in which one strand is DNA and the other strand is RNA are referred to as "hybrid duplexes." As will discussed in more detail below, double-stranded target nucleic acids according to the invention are "duplexes."

5.2.1 Double-Stranded Target Nucleic Acid

As its name implies, the double-stranded target nucleic acid comprises, at a minimum, two strands that are associated with one another via interstrand base pairing interactions. Thus, the double-stranded target nucleic acids of the invention are to be distinguished from single-stranded nucleic acids that have regions of double-strandedness by virtue of intrastrand base-pairing interactions (such as, for example, a tRNA). The double-stranded target may comprise three or more strands or may include regions of triple-strandedness, but preferably do not.

The double-stranded target nucleic acid may have blunt ends, such as when each strand comprises the same number of nucleobases, or it may contain regions of single-strandedness at one or both termini, such as a restriction fragment which has been excised from a longer nucleic acid with endonucleases that leave sticky ends. Preferably, any single-stranded overhangs are relatively short compared to the overall length of the double-stranded target, and are typically in the range of 1–8 nucleotides.

Each strand of the double-stranded target nucleic acid may be composed entirely of deoxyribonucleotides, entirely of ribonucleotides, or may be composed of mixtures of deoxy- and ribonucleotides. Thus, the double-stranded target may be, for example, a DNA/DNA homoduplex, a DNA/RNA hybridduplex or an RNA/RNA homoduplex. Moreover, each strand may comprise mixtures of ribo and deoxyribo nucleotides. Due to their availability in nature and the prevalence of PCR amplification products, the double-stranded target nucleic acid will typically be a double-stranded DNA (DNA/DNA homoduplex) such as an isolated gene or gene fragment or a PCR amplification product ("PCR amplicon").

The strands of the double-stranded target may be composed of the naturally occurring encoding nucleobases (A, C, G, T and U) or modified or synthetic nucleobases, or a combination of both. Common modified or synthetic nucleobases of which the target nucleic acid may be composed include 3-methlyuracil, 5,6-dihydrouracil, 4-thiouracil, 5-bromouracil, 5-thorouracil, 5-iodouracil, 6-dimethyl amino purine, 6-methyl amino purine, 2-amino purine, 2,6-diamino purine, 6-amino-8-bromo purine, inosine, 5-methyl cytosine, 7-deazaadenine, and 7-deaza guanosine. Additional non-limiting examples of modified or synthetic nucleobases of which the target nucleic acid may be composed can be found in Fasman, CRC PRACTICAL HANDBOOK OF BIOCHEMISTRY AND MOLECULAR BIOLOGY, 1985, pp. 385–392; Beilstein's Handbuch der Organischen Chemie, Springer Verlag, Berlin and Chemical Abstracts, all of which provide references to publications describing the structures, properties and preparation of such nucleobases.

As will be recognized by those of skill in the art, many of the above-described modified or synthetic nucleobases are capable of forming Watson-Crick base pairing interactions with the naturally occurring encoding nucleobases A, T, C, G and U. However, as will be described in more detail below, in certain embodiments of the invention, it may be desirable to include in the double-stranded target synthetic nucleobases which are not capable of forming Watson-Crick base pairs with other nucleobases (such as the naturally occurring encoding nucleobases A, T, C, G, and U and common modified nucleobase), but that are capable of forming non-standard (i.e., non-Watson-Crick) base pairs with one another. Nucleobases having these properties are referred to herein as "non-standard synthetic" nucleobases. Examples of such non-standard synthetic nucleobases include, but are not limited to, iso-guanine (iso-G), iso-cytosine (iso-C), xanthine (X), kappa (K), nucleobase H, nucleobase J, nucleobase M and nucleobase N (see U.S. Pat. No. 6,001,983). These non-standard synthetic nucleobases base-pair with one another to form the following non-standard base pairs: iso-C•iso-G, K•X, H•J and M-N. Each of these non-standard base pairs has three hydrogen bonds. Additional non-standard synthetic nucleobases, as well as methods for their synthesis and methods for incorporating them into nucleic acids are found in U.S. Pat. Nos. 5,432,272, 5,965,364 and 6,001,983, the disclosures of which are incorporated herein by reference.

While the backbones of the strands of the target nucleic acid will typically be composed entirely of "native" sugar phosphodiester interlinkages, they may contain one or more modified interlinkages, such as one or more sugar phosphorothioate, sugar phosphorodithioate, sugar phosphoramidate or other modified interlinkages. Additional examples of modified nucleobase interlinkages that can comprise the target nucleic acid, as well as methods for their synthesis, can be found, for example, in Uhlman & Peyman, 1990, Chemical Review 90(4):544–584; Goodchild, 1990, Bioconjugate Chem. 1(3):165–186.

As the methods of the invention capitalize on the kinetic and/or thermodynamic advantages of heteroduplex formation, it will be understood that neither strand of the double-stranded target nucleic acid should comprise a combination of nucleobase interlinkages (i.e., a backbone) that has a net positive charge or net neutral charge at the pH and temperature of the assay. Targets in which one or both strands have backbones bearing a net positive or net neutral charge will tend to have thermostabilites that are too high to be efficiently dissociated and hybridized with a competitor oligo according to the methods of the invention. Thus, while each strand of the double-stranded target may include one or more positively charged or uncharged nucleobase interlinkages, the strand which includes these interlinkages should have a net negative charge at the pH and temperature of the assay. Preferably, each strand of the double-stranded target nucleic acid will have a native sugar phosphodiester backbone.

The double-stranded target nucleic acid may be artificially constructed or isolated from nature. Non-limiting examples of artificially constructed double-stranded target nucleic acids include chimaeric nucleic acids created by splicing nucleic acids from different sources into one nucleic acid (e.g., an artificially constructed plasmid), cDNA sequences reverse-transcribed in vitro from an RNA template, amplicons created using PCR or other amplification techniques, and nucleic acids synthesized chemically. Non-limiting examples of naturally occurring double-stranded target nucleic acids include naturally occurring plasmids or portions thereof, genomic DNA or portions thereof, and DNA derived from subcellular organelles, all of which may be employed in the methods of the invention without prior isolation or purification, or, preferably, are isolated and prepared for use with the present invention using methods known in the art.

The double-stranded target nucleic acid can be virtually any number of base pairs in length, from tens to several hundred, to several thousand, or even more. For example, the double-stranded target nucleic acid may be a complete gene, several genes or even a whole chromosome. However, as practicing the invention requires complete dissociation of the strands of at least a fraction of the target molecules present in the sample, those of skill in the art will recognize that the double-stranded target nucleic acid will preferably be of a length that permits efficient strand dissociation. While the extent of dissociation and the conditions under which dissociation may be achieved will depend, in part, upon the nucleobase composition (e.g., C+G content) target nucleic acids for use in the present invention will typically be between about 30 and 2000 base pairs in length, preferably between about 40 and 500 base pairs in length and more preferably between about 60 and 200 base pairs in length. Where the target nucleic acid is longer, for example a whole gene, it can be conveniently fragmented to a preferred size using conventional techniques such as sonication, shearing and endonuclease digestion. A specific fragment may be isolated and used as the target in the methods described herein, or the entire fragmentation products may be used without purification.

The target nucleic acid may be modified to include a reporter group or moiety which can be used, for example, to detect hybridization between the target and competitor oligo, for further purification post-hybridization or for other purposes as will be apparent to those having skill in the art. Useful reporter groups include radioisotopes, non-radioisotopes, moieties that emit light, such as fluorophores and moieties that chemiluminesce, moieties that adsorb light, such as chromophores, ligands capable of binding to a secondary reporter group (e.g., biotin), enzymes capable of producing a colorimetric reaction (e.g. peroxidases, digoxygenine), and the like.

Alternatively, the target nucleic acid may be modified to include a moiety that facilitates capture and/or isolation of the strands of the dissociated target nucleic acid following contact with the competitor oligo. A variety of such moieties are discussed infra in connection with embodiments of the invention employing capture probes and include, for example, binding molecules such as biotin, solid supports and capture sequences. Any of these moieties may be included in the target nucleic acid. Preferably, only one strand of the target will include such a moiety, or each strand will include a different moiety, such that the different moieties can be used to readily separate or isolate the dissociated strands from one another.

Methods and reagents for incorporating such reporter and/or capture moieties into nucleic acids are well-known in the art, as are methods for detecting such reporter groups. The actual reporter and/or capture moiety used will depend, of course, on the desired application, quantity of target nucleic acid and other factors that will be apparent to those having skill in the art.

The nucleobase sequence of the double-stranded target may be exclusively native (i.e., derived exclusively from the organism from which the target is obtained), exclusively engineered or a mixture of native and engineered sequences. Examples of targets having exclusively native sequences include target nucleic acids isolated from naturally-occurring organisms, etc. Examples of targets comprising both native and engineered sequence include PCR amplicons that have been engineered to include restriction enzymes sites, recognition sequences (e.g., zip-codes, universal priming sites, etc.), etc. The engineered portion of the target may be either an internal sequence or at one or both termini.

Figure 2:
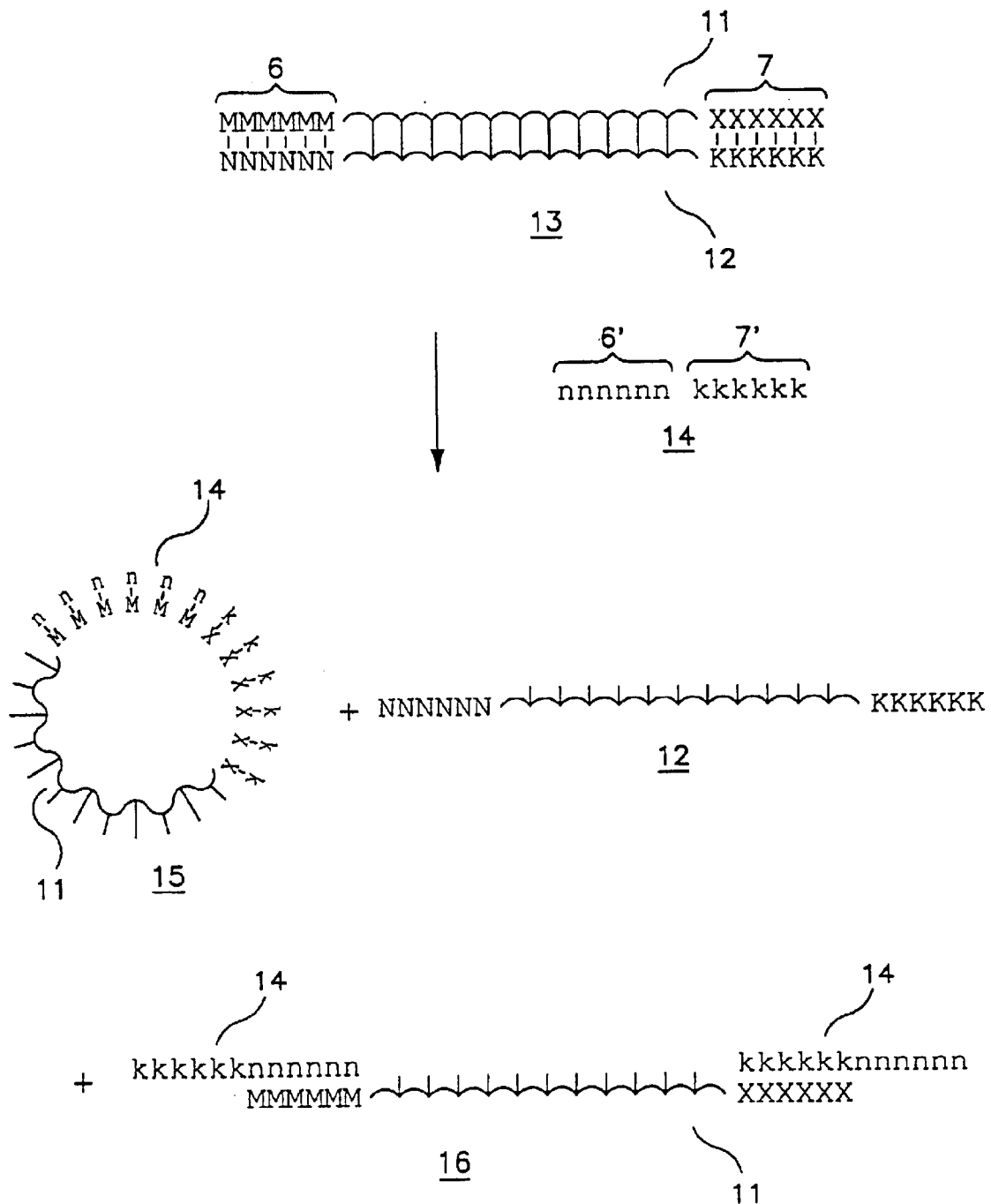
FIG. 2 illustrates an embodiment of the invention in which the competitor oligo comprises two contiguous nucleobase sequences, one complementary to a first target tail sequence and another complementary to a second target tail sequence, that are connected to one another via a spacer.
Figure 3:
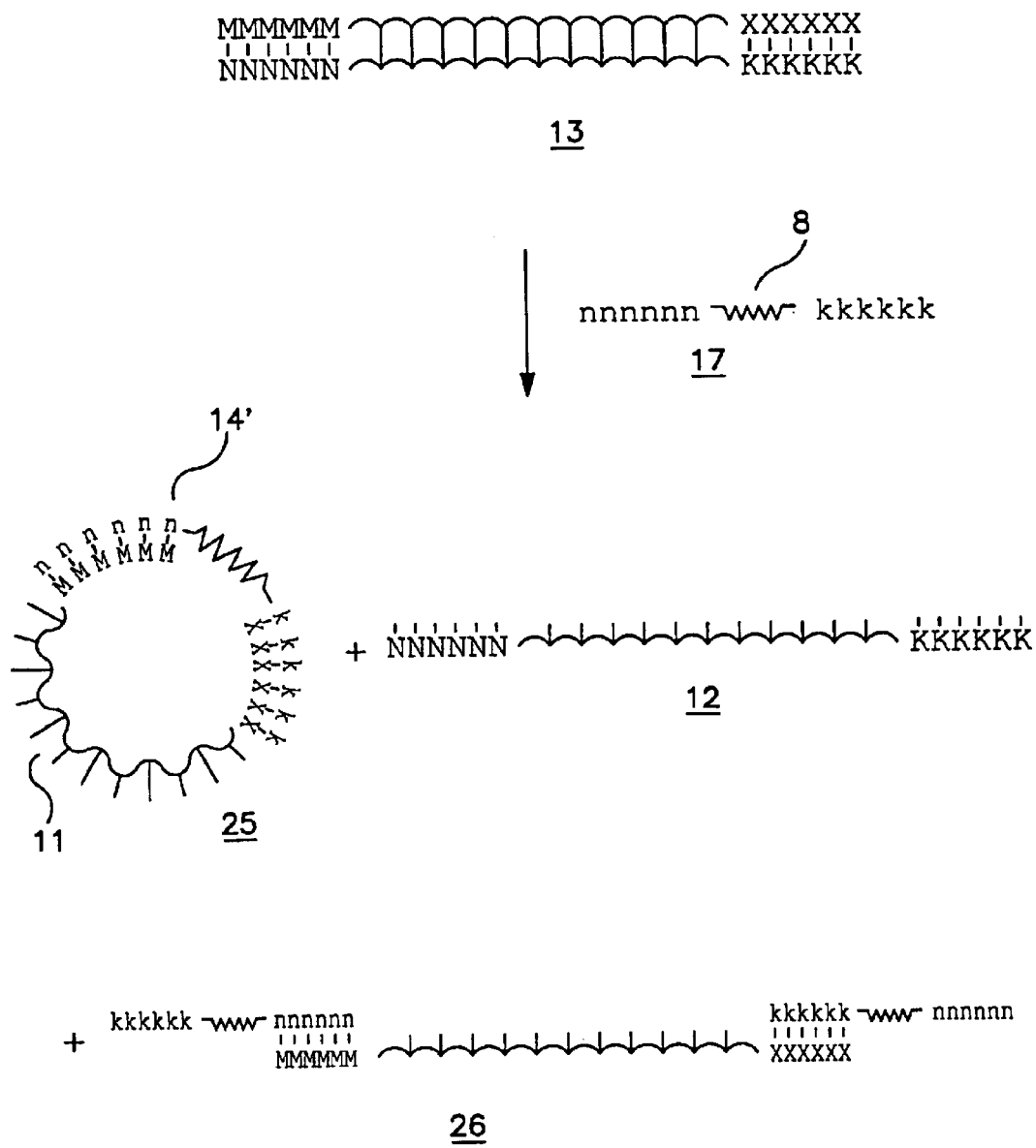
FIG. 3 illustrates an embodiment of the invention in which the competitor oligo comprises a linker and two nucleobase sequences, one complementary to a first target tail sequence and another complementary to a second target tail sequence.

In one embodiment of the invention, the double-stranded target nucleic acid includes one or more engineered tail sequences. As used herein, a "tail sequence" is a stretch of known nucleobase sequence that is positioned at a terminus of a strand of the double-stranded target nucleic acid. Either or both of the strands of the target may include the same or different tail sequences, and they may be included at either or both termini. Typically, the tail sequence is completely complementary to the competitor oligo and uncomplementary to internal sequences of the target nucleic acid. The tail sequence may be used to facilitate capture of the dissociated strands of the double-stranded target nucleic acid or for hybridization of the competitor oligo as illustrated in FIGS. 2 and 3. In a preferred embodiment, the tail sequence is composed of non-standard synthetic nucleobases, as previously described. Referring to FIG. 2, which illustrates the method of the invention with a target nucleic acid comprising two tail sequences (6 and 7) composed of non-standard synthetic nucleobases, when non-standard tail sequences are employed, the competitor oligo also comprises non-standard synthetic nucleobases. Since these non-standard synthetic nucleobases do not form standard Watson-Crick base pairs, the competitor oligo 14 is capable of hybridizing only to the tail sequences of first strand 11. Thus, utilizing non-standard synthetic tail sequences provides the advantage of decreased cross-reactivity, as well as other advantages as will be apparent to those of skill in the art.

Tail sequences may be added to or engineering into a target nucleic acid using any technique known in the art. For example, tail sequences can be added using appropriate PCR primers in a PCR amplification (see Sambrook et al., supra) as is well known in the art. According to this method, a PCR primer is selected that has a sequence at its 3' end that is complementary to one end of a nucleic acid of interest. The 5' end of the primer comprises the tail sequence. A second primer is selected that has a sequence at its 3' end that is complementary to the other end of the nucleic acid of interest. These two primers are used to amplify the nucleic acid of interest. The resulting amplicon comprises a target nucleic acid having tail sequences at its termini.

The tail sequence also may be added using standard cloning techniques (see Sambrook et al., supra). For example, a synthetic double-stranded polynucleotide comprising a tail sequence may be engineered to include a sticky end or may be cut with a restriction enzyme, leaving it with a sticky end. The nucleic acid of interest can be cut with a restriction enzyme that leaves it with a complementary sticky end. The restriction-digested polynucleotide and nucleic acid of interest may then be ligated together to create a target nucleic acid comprising a tail sequence. Alternatively, if the double-stranded polynucleotide and the nucleic acid of interest each have blunt ends, they may be ligated togther without digestion with a restriction enzyme. Blunt ends can also be created on the double-stranded nucleic acid of interest and/or the polynucleotide using a restriction enzyme that creates blunt ends, if they contain the appropriate restriction sites at the appropriate locations.

Tail sequences composed of non-standard synthetic nucleobases can also be conveniently obtained using standard cloning techniques. According to this method a synthetic double-stranded polynucleotide having a single-stranded overhang or sticky end is ligated to a double-stranded nucleic of interest that has a complementary overhang or sticky end. The duplex region of the polynucleotide comprises the non-standard synthetic tail sequence and the overhang comprises naturally occurring encoding nucleotides. Annealing the overhang polynucleotide to the double-stranded nucleic of interest yields a complex that can be ligated according to conventional means to yield a target nucleic acid comprising a non-standard synthetic tail sequence. Alternatively, tail sequences comprising non-standard synthetic nucleobases may be prepared using enzymatic gap-filling reactions with appropriate non-standard synthetic nucleoside triphosphates according to known techniques.

Other methods of introducing tail sequences into the target nucleic acid will be apparent to those having skill in the art.

The tail sequence can be any number of nucleotides in length and may comprise any nucleobase composition, but will typically be of a length and composition that permits efficient hybridization under the relevant conditions. Preferably, a tail sequence comprises between 5 and 50 nucleotides and more preferably between 7 and 20 nucleotides, and is composed of non-standard synthetic nucleobases, as previously described. When composed of naturally occurring encoding nucleobases and/or modified nucleobases, the C+G content is not critical, and can vary over quite a wide range.

A tail sequence may be designed to have simultaneously a number of desirable features (e.g., high G-C content for stronger hybridization, high sequence complexity for more discriminating hybridization, multiple restriction enzyme recognition sites for ease of manipulation, etc.). Tail sequences having appropriate characteristics for a particular application will be apparent to those having skill in the art. The use of a tail sequence is advantageous because it allows for the identification, purification, and/or isolation of the strand of the nucleic acid comprising it via the use of hybridization techniques that are well-known in the art. The use of multiple different tail sequences permits complex manipulations of the strands of the double-stranded target nucleic acid. Tail sequences composed of the preferred non-standard synthetic nucleobases are particularly advantageous, as their orthogonality with the naturally occurring encoding nucleobases reduces hybridization cross reactivity during successive hybridization steps.

In a particularly preferred embodiment, the double-stranded target nucleic acid includes a universal tail sequence. As used herein, a "universal tail sequence" is a tail sequence comprising features that make it generally useful for many different applications. Generally, a universal tail sequence is of a sufficient length and complexity such that it has a low probability of occurring in nature (i.e., on the order of 18 to 50 nucleotides, preferably 10 to 30 nucleotides), and therefore would not be expected to be complementary to nucleic acids isolated from organisms. Owing to their inability to form standard Watson-Crick base pairs, universal tail sequences comprising non-standard synthetic universal tail sequences would not readily hybridize with nucleic acids isolated from organisms. Thus, tail sequences composed of such non-standard synthetic nucleobases may typically be shorter than those composed of nucleobases capable of forming Watson-Crick base pairs without compromising specificity. Thus, highly specific Universal tail sequences composed of these non-natural synthetic nucleobases as short as 6–8 nucleobases may be readily designed.

Including a universal tail sequence in the target nucleic acid facilitates the manipulation and isolation of the desired strand of the target. If the same universal tail sequence is added to each of a plurality of double-stranded target nucleic acids, then the desired strand of each target may be isolated using the same "universal" complementary competitor oligo. Thus, including a universal tail sequence in a target nucleic acid obviates the need to synthesize unique competitor oligos for individual applications. A single universal competitor oligo that is complementary to the universal tail sequence can be used to isolate one strand of any target nucleic acid. Targets including universal tail sequences may be readily generated in PCR reactions using "universal" primers, as will be apparent to those having skill in the art, or through standard cloning techniques, as previously described.

For example, to create a double-stranded target including a universal tail sequence, a "universal" PCR primer may be synthesized having a sequence of nucleotides that is complementary to the target nucleic acid at its 3' end and a universal tail sequence at its 5' end. PCR amplification of a template nucleic acid of interest and another appropriate primer will produce a target nucleic acid molecule comprising a universal tail sequence.

In a preferred embodiment, the double-stranded target nucleic acid includes a tail sequence at each terminus. Such target nucleic acids generally have the following structure (I):

5'-TAIL1-SEQUENCE-TAIL2-3'

3'-TAIL1'-SEQUENCE'-TAIL2'-5' wherein "TAIL1" represents a first, optionally universal, tail sequence; "TAIL2" represents a second, optionally universal, tail sequence; "SEQUENCE" represents a nucleotide sequence corresponding to, or obtained or derived from, the nucleic acid of interest (i.e., the nucleic acid from the target organism); "TAIL1'" represents a sequence that is complementary to TAIL1, "TAIL2'" represents a sequence that is complementary to TAIL2; and SEQUENCE' represents a sequence that is complementary to SEQUENCE. In structure (1), the dashes between the various TAILs and SEQUENCEs represents covalent linkages. The sequences of TAIL1 and TAIL2 may be the same or different. Preferably, TAIL 1 and TAIL 2 are different universal tail sequence.

An exemplary embodiment of the invention in which the double-stranded target nucleic acid is a construct according to structure (I) is illustrated in FIG. 2. Referring to FIG. 2, target nucleic acid 13 comprises first and second strands 11 and 12, respectively. First strand 11 comprises a first 5'-tail sequence 6 and a second, different 3'-tail sequence 7. As illustrated, the tail sequences are composed of non-standard synthetic nucleobases, although other nucleobases, such as the naturally occurring encoding nucleobases, could be used. Target 13 is contacted with competitor oligo 14, which comprises a first nucleobase sequence 6' that is complementary to first tail sequence 6 and a second nucleobase sequence 7' that is complementary to second tail sequence 7. Target 13 and competitor oligo 14 are contacted under conditions in which target 13 dissociates and first strand 11 hybridizes with competitor oligo 14, forming dissociated second strand 12, circular heteroduplex 15 and ternary complex 16. Higher order complexes in which one or more first strands 11 hybridize with the single stranded portions of ternary complex 16 may also form, but are not illustrated. Any or all of the various different molecules 15, 16 and 12 may be isolated from one another and a strand of the double-stranded target 13 isolated therefrom, as will be described in more detail, below. For example, dissociated strand 12 may be readily isolated with a capture probe complementary to a portion of 12.

5.2.2 Competitor Oligo

The competitor oligo comprises a series of nucleobases covalently attached to a backbone having a net positive or neutral charge at the pH and temperature of the assay. The nucleobases comprising the competitor oligo may be the naturally occurring encoding nucleobases, modified nucleobases, synthetic nucleobases or non-standard synthetic nucleobases, or a combination of any of these nucleobases, as previously described in connection with the target nucleic acid. The only requirement for the nucleobases of the competitor oligo is that they be capable of forming base pairs with the nucleobases comprising a region of the target nucleic acid. For example, if the competitor oligo is designed to hybridize with a region of the target nucleic acid that is composed of the naturally occurring encoding nucleobases, the competitor oligo should comprise a complementary sequence of nucleobases that are capable of forming Watson-Crick-type base pairs. If the competitor oligo is designed to hybridize with, for example, a universal tail sequence composed of the preferred non-standard synthetic nucleobases, then the competitor oligo should comprise a complementary sequence of non-standard synthetic nucleobase. The degree of complementary required will be discussed more thoroughly in a later section.

The backbone connecting the nucleobases may be any polymer known in the art that meets four criteria. First, when included in a competitor oligo, the backbone should bear a net positive or neutral charge at the pH and temperature of the assay, typically pH 6 to pH 8 and about 20° C. to about 40° C. Second, the backbone should be amenable to the covalent attachment of nucleobases. Third, the geometry of the covalently attached nucleobases (i.e., the distances between them, and their orientation relative to each other), should allow them to base pair with the nucleobases of a complementary nucleic acid strand. Preferably, the geometry of the covalently attached nucleobases will approximate the geometry of nucleobases in natural nucleic acids (e.g., DNA or RNA). Fourth, the backbone should be flexible enough to permit hybridization between the competitor oligo and a complementary nucleic acid strand.

A variety of nucleobase interlinkages that, when used alone or in combination, will yield competitor oligos having backbones that satisfy the above-described criteria are known in the art. For example, nucleobase polymers having positively charged sugar-guanidyl interlinkages are described in U.S. Pat. No. 6,013,785 and U.S. Pat. No. 5,696,253 (see also, Dagani, 1995, Chem. & Eng. News 4–5:1153; Dempey et al., 1995, J. Am. Chem. Soc. 117:6140–6141). Analogues in which the sugar is 2'-deoxyribose are referred to as "DNGs," whereas those in which the sugar is ribose are referred to as "RNGs." Examples of nucleobase polymers having a positively charged polyamide backbone with alkylamine side chains are described in U.S. Pat. No. 5,786,461; U.S. Pat. No. 5,766,855; U.S. Pat. No. 5,719,262; U.S. Pat. No. 5,539,082 and WO 98/03542 (see also, Haaima et al., 1996, Angewandte Chemie Int'l Ed. in English 35:1939–1942; Lesnik et al., 1997, Nucleosid. Nucleotid. 16:1775–1779; D'Costa et al., 1999, Org. Lett. 1:1513–1516 see also Nielson, 1999, Curr. Opin. Biotechnol. 10:71–75).

Nucleobase polymers having uncharged backbones have also been described in the art. For example, nucleobase polymers having uncharged polyamide backbones are described in WO 92/20702 and U.S. Pat. No. 5,539,082. Nucleobase polymers having uncharged morpholino-phosphoramidate backbones are described in U.S. Pat. No. 5,698,685, U.S. Pat. No. 5,470,974, U.S. Pat. No. 5,378,841 and U.S. Pat. No. 5,185,144 (see also, Wages et al., 1997, BioTechniques 23:1116–1121).

Additional nucleobase interlinkages which may comprise the competitor oligo include, but are not limited to, peptide-based nucleic acid mimetic interlinkages (see, e.g., U.S. Pat. No. 5,698,685), carbamate interlinkages (see, e.g., Stirchak & Summerton, 1987, J. Org. Chem. 52:4202), amide interlinkages (see, e.g., Lebreton, 1994, Synlett. February, 1994:137), methylhydroxyl amine interlinkages (see, e.g., Vasseur et al., 1992, J. Am. Chem. Soc. 114:4006), 3'-thioformacetal interlinkages (see, e.g., Jones et al., 1993, J. Org. Chem. 58:2983) and sulfamate interlinkages (see, e.g., U.S. Pat. No. 5,470,967) as well as the various modified interlinkages discussed in connection with the target nucleic acid, supra.

All of the above-listed references relating to the various interlinkages are incorporated herein by reference. As previously discussed, the backbone of the competitor oligo should have a net positive or net neutral charge at the intended pH and temperature of use. Those of skill in the art will recognize that competitor oligos that have a net positive charge may include nucleobase interlinkages that are negatively charged, such as native sugar phophodiester interlinkages, so long as the net charge of the competitor oligo backbone is positive. This can be conveniently accomplished by including a majority of positively charged interlinkages.

When using a net positively charged competitor oligo, care should be taken to insure that the magnitude of the charge of the backbone does not become too large. If the charge is too large, the interaction of the competitor oligo with the target nucleic acid will be ionic in nature and the competitor oligo will tend to lose its sequence specificity (i.e., the competitor oligo will tend to act as an ion exchange resin). For competitor oligos of most lengths, sequence specificity can be readily retained by insuring that the net positive charge of the backbone does not exceed about 5–6. Preferably, the net positive charge of the backbone should not exceed about 1–3.

When the competitor oligo backbone includes positively charged interlinkages such that is has a net positive charge, the other nucleobase interlinkages are preferably neutral interlinkages, such as neutral polyamide interlinkages or neutral morpholino-phosphoramidate interlinkages or a combination thereof. Use of such neutral interlinkages avoids or reduces the local interstrand charge-charge repulsions that might be experienced with heteroduplexes in which the competitor oligo includes negatively charged nucleobase interlinkages such as sugar phophodiester interlinkages.

In a preferred embodiment of the invention, the competitor oligo comprises neutral nucleobase interlinkages, such as the neutral amide and morpholino-phosphoramidate interlinkages previously described, and optionally includes from about 1 to about 3–4 positively charged interlinkages. The neutral interlinkage may all be the same, or they may be different. For example, the competitor oligo may include some morpholino-phosphoramidate interlinkages and some neutral amide interlinkages. Within each class, the various morpholino-phosphoramidate and neutral amide interlinkages may also be the same or different. The optional positively charged interlinkages may also be the same or different.

In a particularly preferred embodiment of the invention, the competitor oligo is a neutral polyamide nucleic acid ("PNA"). As used herein, "PNA" refers to a polymer of nucleobases linked together via an uncharged polyamide backbone. The PNA backbone may be any backbone of acyclic, achiral and neutral polyamide linkages to which nucleobases can be attached and that satisfies the criteria discussed supra. PNAs useful in the present methods are described, for example, in U.S. Pat. No. 5,539,082 and WO 92/20702, the disclosures of which are incorporated herein by reference. The amino acids which form the polyamide backbone may be identical or different, but are preferably identical. Particularly preferred PNAs are those in which the nucleobases are attached to an N-(2-aminoethyl)-glycine backbone, i.e., a peptide-like, amide-linked unit (see, e.g., U.S. Pat. No. 5,719,262; Buchardt et al., 1992, WO 92/20702; Nielsen et al., 1991, Science 254:1497–1500). A partial structure of such a particularly preferred N-(2-aminoethyl)-glycine PNA is illustrated in structure (II), below:

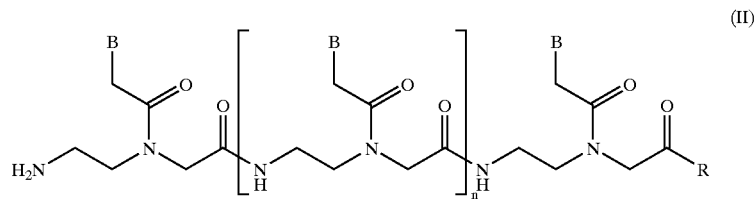

(II)

wherein:

n is an integer that defines the length of the N-(2-aminoethyl)-glycine PNA, as will be more thoroughly discussed below;

each B is independently a nucleobase; and

R is —OR' or —NR'R', where each R' is independently hydrogen or ($C_1$–$C_6$) alkyl, preferably hydrogen.

As will be recognized by those having skill in the art, in the competitor oligos described herein, e.g. the preferred PNAs, the nucleobases, whether natural, modified or synthetic, are attached to the backbone in an orientation that permits the nucleobases to base-pair with the desired strand of the target nucleic acid. For natural and modified nucleobases, this is typically at the same position found in nature, i.e., the N9 position for adenine, guanine and inosine, and the N1 position for thymine, cytosine, uracil, dihydrouridine (D), pseudouridine (ψ) etc. The non-standard synthetic nucleobases are also typically attached to the backbone via the N1 position for the pyrimidine non-standard synthetic bases and N9 position for the purine non-standard synthetic bases (see U.S. Pat. No. 6,001,983 and U.S. Pat. No. 5,965,364). Points of attachment for other nucleobases will be apparent to those of skill in the art.

The competitor oligo may be synthesized using any of a number of conventional methods that are well-known in the art. The methods used will depend, in part, upon the specific nucleobase interlinkages selected. Methods for synthesizing oligos comprising specific linkages are provided in the various patents and publication listed in connection with each specific type of linkage, supra. For example, suitable methods for synthesizing competitor oligos comprising positively-charged sugar guanidyl interlinkages are described in U.S. Pat. No. 6,013,785 and U.S. Pat. No. 5,696,253. Suitable methods for synthesizing competitor oligos comprising positively-charged amide interlinkages are described, for example, in U.S. Pat. No. 5,786,461, U.S. Pat. No. 5,766,855, U.S. Pat. No. 5,719,262 and WO 98/03542. Suitable methods for synthesizing competitor oligos comprising neutral morpholino interlinkages are described in U.S. Pat. No. 5,185,444 and U.S. Pat. No. 5,142,047. Suitable methods for synthesizing competitor oligos comprising neutral amide interlinkages, such as the particularly preferred N-(2-aminoethyl)-glycine PNAs, are described, for example, in U.S. Pat. No. 5,539,082 and WO 92/20702. All of the above-listed patents and references are hereby incorporated by reference. Competitor oligos comprising combinations of different interlinkages may be synthesized by routine modification of the above-listed methods and/or by well-known methods.

The competitor oligo must be capable of hybridizing to a region or portion of the first strand of the double-stranded target nucleic acid under the desired hybridization assay conditions. Thus, the competitor oligo must be at least partially complementary to a region or portion of the first strand of the target, depending on the requirements of the particular application. The region of complementarity may be to an internal target sequence, as illustrated in FIG. 1, or it may be to one or more terminal target sequences, as illustrated in, e.g., FIG. 2. By "complementary" it is meant that the nucleobases of the competitor oligo form base pairs with the nucleobases of the target strand. For the naturally occurring encoding nucleobases and many modified or synthetic bases, the base-pairing interactions will follow normal Watson-Crick rules. However, the non-standard synthetic nucleobases described, e.g., in U.S. Pat. No. 5,432,272 and U.S. Pat. No. 5,965,364 (for example bases iso-C, iso-G, K, X, H, J, M and N) form non-standard (i.e., non-Watson-Crick) base pairs. These non-standard bases typically base pair with one another as follows: iso-C•iso-G, K•X, H•J and M•N (each base pair typically has three hydrogen bonds). Base pairing schemes for additional non-standard synthetic bases are illustrated in U.S. Pat. No. 5,432,272, FIG. 4. It will be understood that all of these base-pairing interactions, whether standard Watson-Crick or non-standard, are intended to fall within the scope of "complementary" as that term is used herein.

The degree of complementarity will depend upon the nature of the assay. For example, where it is desirable to isolate one strand from each member of a family of polymorphic double-stranded target nucleic acids, the competitor oligo may, by design, have regions of non-complementarity—typically centered around the regions containing the polymorphism. Thus, the degree of complementarity is not critical to the success of the method—all that is required is a degree of complementarity that is sufficient to achieve the desired result. For many applications, such as those in which it is desirable to isolate one strand of a distinct target nucleic acid from amongst a plurality of different target nucleic acids, the sequence of the competitor oligo will preferably be completely complementary to a region or portion of the desired strand of the double-stranded target. In this embodiment, the competitor oligo will preferably be completely complementary to a region or portion of the target that is unique, thereby permitting specific isolation of the complementary strand of the target from a plurality of target nucleic acids. Thus, the degree of complementarity will depend upon the desired application and will be apparent to those of skill in the art.

In embodiments in which the target nucleic acid includes one or more tail sequences, such as the embodiments illustrated in FIGS. 2 and 3, the sequence of the competitor oligo will preferably be completely complementary to a tail sequence of the target. In embodiments in which the target nucleic acid includes two terminal tail sequences, the competitor oligo preferably comprises two sequences—one completely complementary to the first tail sequence and one completely complementary to the second tail sequence, as illustrated in FIGS. 2 and 3.

Those of skill in the art will appreciate that many competitor oligos, and especially the particularly preferred N-(2-aminoethyl)-glycine PNAs, can hybridize with a complementary DNA or RNA in either a parallel or antiparallel orientation (see, e.g., Egholm et al., 1993, Nature 365:566–568). The orientation is said to be antiparallel when the carboxyl terminus of the PNA is directed towards the 5'-end of the DNA or RNA and the amino terminus of the PNA is directed towards the 3'-end of the DNA or RNA. In the parallel orientation, the carboxyl and amino termini of the PNA are reversed with respect to the 5' and 3' ends of the DNA or RNA. Thus, those of skill in the art will appreciate that the nucleobase sequence of the competitor oligo will depend upon whether parallel or antiparallel hybridization with the target nucleic acid is desired. As hybridization in an antiparallel orientation is typically more stable than parallel hybridization, the sequence of the competitor oligo will preferably be chosen such that it will hybridize with the desired strand of the double-stranded target nucleic acid in an antiparallel orientation.

While the competitor oligo will often be comprised of a contiguous stretch of nucleobases, it need not be. Stretches of nucleobases may be interrupted by one or more spacer moieties that do not participate in sequence-specific base pairing interactions with the target nucleic acid. An embodiment of the invention in which the competitor oligo comprises a spacer moiety is illustrated in FIG. 3, and is discussed in more detail, below. The spacer moiety may be long or short, hydrophobic or hydrophilic or flexible, semi-rigid or rigid, depending on the desired application. A variety of spacer moieties useful for spacing one molecule from another, or for spacing a molecule from a solid surface, have been described in the art; all of these spacer molecules may be used to space regions of the competitor oligo from one another.

Figure 9:
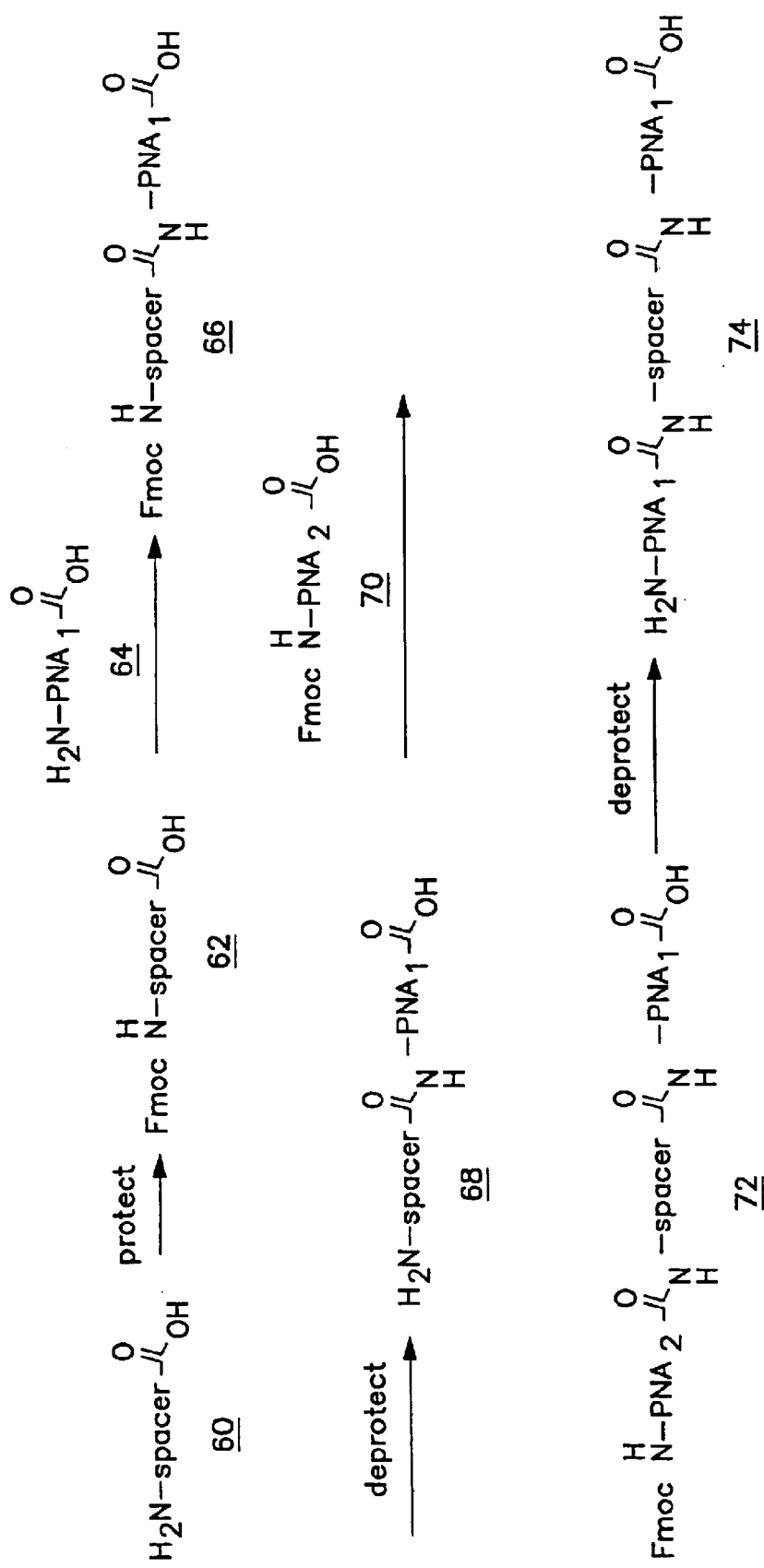
FIG. 9 illustrates an exemplary scheme for synthesizing a competitor oligo including a spacer moiety.

For example, for the preferred PNA competitor oligos, the spacer may comprise a peptide, such as polyalanine (flexible) or polyproline (rigid). To create the peptide spacer, the individual amino acids comprising the spacer may be added during the synthesis of the PNA using conventional peptide synthesis chemistries. Alternatively, the peptide spacer may be condensed with the PNA segments comprising the competitor oligo, as illustrated in FIG. 9. Referring to FIG. 9, the N-terminus of spacer peptide 60 is protected, for example with Fmoc, to yield N-protected spacer 62 according to conventional techniques. N-protected spacer 62 is condensed with first PNA segment 64 using standard coupling chemistry to yield N-protected intermediate 66. N-protected intermediate 66 is deprotected to yield intermediate 68, which is then condensed with N-protected second PNA segment 70, again using standard coupling chemistry, to yield N-protected competitor oligo 72. Deprotection of 72 yields competitor oligo 74, which includes a peptide spacer. Any reactive side chains on spacer 60 may also be protected using well-known protecting groups and chemistries (see, e.g., Green & Wuts, Protective Groups in Organic Synthesis, 2d Ed., 1991, John Wiley & Sons, Inc.).

Competitor oligos having non-peptide spacers may also be synthesized as illustrated in FIG. 9. For example, any molecule which has both an amino and carboxyl group, such as, for example, a β-amino acid, a γ-amino acid, an amino alkylacid (e.g., 4-amino butyric acid, 5-amino pentanoic acid, 6-amino caproic acid, etc.) may be used in place of compound 60 to ultimately yield a competitor oligo comprising a spacer moiety. Additional exemplary spacers that can be used to space one region of the competitor oligo from another, as well as methods of synthesizing competitor oligos comprising such spacers, will be apparent to those of skill in the art. For PNA competitor oligos, a preferred spacer is the O-spacer described in Egholm, et al, 1995, Nucl. Acids Res. 23:217–222, incorporated herein by reference.

An embodiment of the invention employing a competitor oligo including a spacer moiety is illustrated in FIG. 3. FIG. 3 is similar to FIG. 2, except that in FIG. 3, the competitor oligo 17 comprises two nucleobase sequences 6' and 7' separated by intervening spacer 8. Like competitor oligo 14 of FIG. 2, the nucleobase sequence 6' is complementary to first tail sequence 6 and nucleobase sequence 7' is complementary to second tail sequence 7 of target 13. Dissociation of target 13 and hybridization with competitor oligo 17 yields circular heteroduplex 25, ternary complex 26 and dissociated second strand 12. As previously discussed for FIG. 2, higher order complexes may form, but are not illustrated. Dissociated second strand 12 and/or complexes 25 and 26 may be separated from one another and a strand of target 13 isolated, as will be described in more detail below.

While the competitor oligo may be any number of nucleobases in length, it will typically comprise a number of nucleobases sufficient to permit rapid and efficient hybridization at the temperatures and ionic strengths used to isolate the strand of the target, while at the same time minimizing the occurrence of secondary structure. Moreover, it should be long enough so that it affords the desired degree of specificity. Of course, as competitor oligos comprised wholly of non-standard synthetic nucleobases are only complementary to other non-standard synthetic nucleobases, the specificity of such competitor oligos may be designed to be independent of length. Selecting a competitor oligo length that exhibits the desired degree of specificity will be apparent to those of skill in the art.

The length of the competitor oligo will also depend, in part, on the length of the target nucleic acid. Preferably, the length of the competitor oligo should be selected so that it can compete favorably against reassociation or re-annealing of the strands of the target nucleic acid under the desired conditions of the assay. Typically, this can be achieved by selecting a competitor oligo that is on the order of about ⅓ to 1 times (in nucleobase units) the length of the target strand to be isolated. Thus, for a target nucleic acid in the range of 50–60 bp in length, competitor oligos ranging in size from about 15–20 up to about 50–60 nucleobases in length should yield good results.

In order to facilitate isolation of the dissociated strands of the double-stranded target, the competitor oligo may be conjugated to, or modified to include, a moiety that facilitates isolation and/or capture ("capture moiety"). In one embodiment, the capture moiety may be a solid support. The use of a competitor oligo that is immobilized on a solid support in the methods of the invention is illustrated in FIG. 6.

Figure 6:
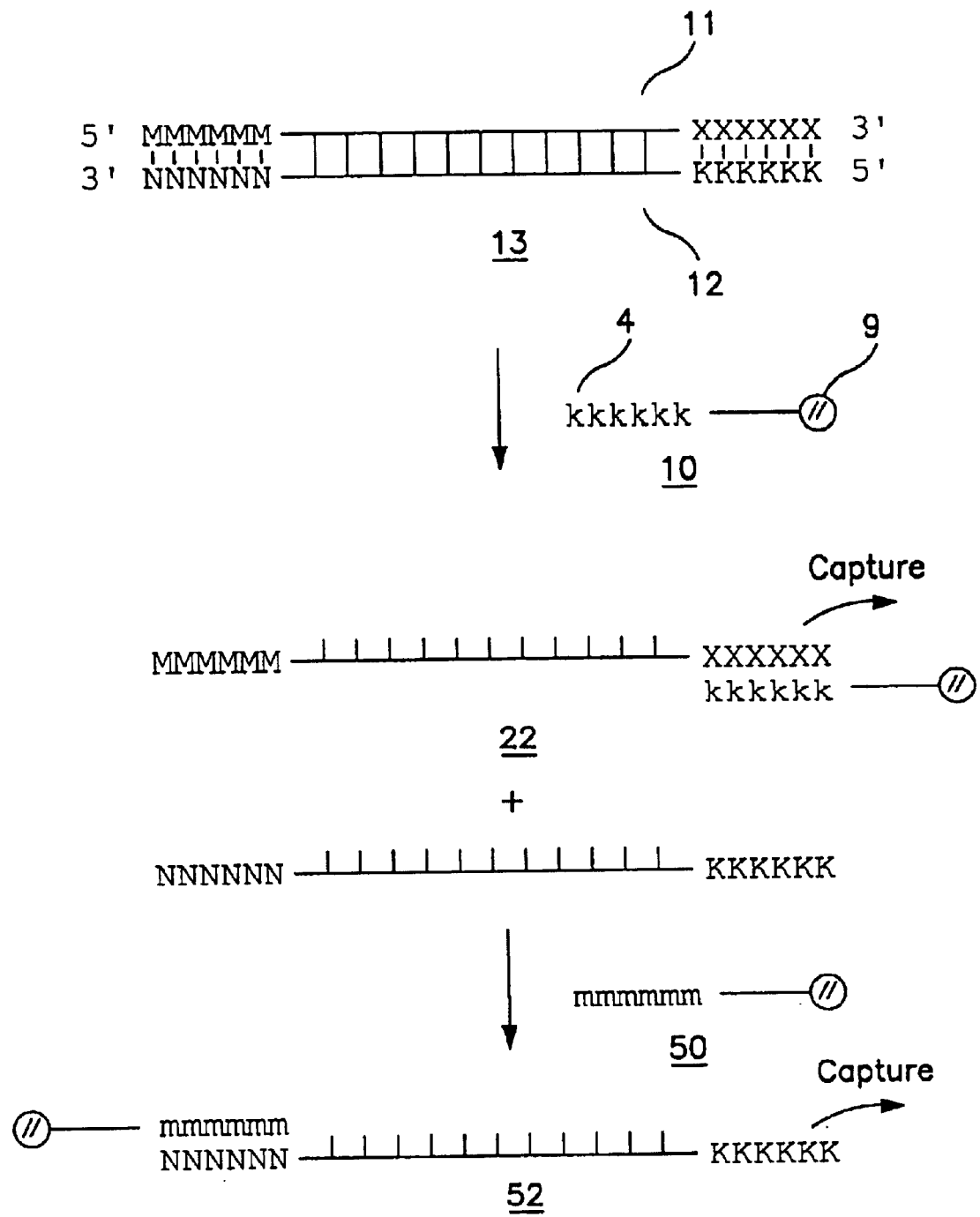
FIG. 6 illustrates an embodiment of the invention in which the competitor oligo includes a solid support capture moiety.

Referring to FIG. 6, double-stranded target nucleic acid 13 is contacted with immobilized competitor oligo 10. Immobilized competitor oligo 10 comprises competitor oligo 4 and solid support 9. As illustrated in FIG. 6, competitor oligo 4 is immobilized on solid support 9 by way of covalent attachment. Other modes of immobilization are discussed below. The contacting is performed under conditions which promote or favor dissociation of double-stranded target 13 into first and second strands 11 and 12, respectively, and hybridization between the first strand 11 and the competitor oligo 4 portion of immobilized competitor oligo 10, thereby forming heteroduplex 22 and dissociated strand 12. Heteroduplex 22 is then isolated or captured from dissociated strand 12 and any double-stranded target 13 by means of solid support 9, such as, for example, by decanting, filtration, centrifugation, etc. If solid support 9 is magnetic, such as a magnetic bead, heteroduplex 22 may be conveniently isolated with the aid of a magnet. Removal of heteroduplex 22 yields second strand 12, which may be used without further purification. If first strand 11 is the desired target strand, heteroduplex 22 can be dissociated and first strand 11 isolated, conveniently by removing immobilized competitor oligo 10 with the aid of solid support 9.

Alternatively, dissociated second strand 12 may be isolated or captured from the mixture (or from the sample after removal of heteroduplex 22) by capture with capture probe 50. Like immobilized competitor oligo 10, capture probe 50 preferably comprises a competitor oligo immobilized on a solid support. However, the nucleobase sequence of capture probe 50 is complementary to a portion of second strand 12. If the solid supports of immobilized competitor oligo 10 and capture probe 50 cannot be readily separated from one another based on a differential property, such as differences in size, shape, magnetism, etc., the capture of heteroduplex 22 and heteroduplex 52 should be performed serially, in either order. Use of a capture probe 50 complementary to second strand 12 permits both strands of target 13 to be easily and efficiently isolated from complex mixtures. Although illustrated in FIG. 6 as a competitor oligo, those of skill in the art will recognize that capture probe 50 may comprise a DNA or RNA sequence. Moreover, the capture moiety need not be a solid support—it can be any capture moiety known in the art, including, for example, biotin. Manipulating the capture conditions for these other types of capture probes will be apparent to those of skill in the art.

Referring to FIG. 6, competitor oligo 4 may be immobilized on, or associated with, solid support 9 by a variety of different mechanisms, including absorption, ionic attraction, hydrophobic interactions and covalent attachment. Alternatively, competitor oligo 4 may be immobilized on solid support 9 through the use of pairs of specific binding compounds, such as biotin and streptavidin.

The support 9 may take a variety of regular or irregular shapes, such as spheres, ellipses, discs, cubes, pyramids, etc. and may be comprised of any material (or mixture of materials) that is suitable for the desired mode of immobilization and that is compatible with, i.e., does not dissolve or otherwise decompose or degrade, under the conditions used to immobilize the competitor oligo or isolate the strand of the double-stranded nucleic acid according to the invention. Suitable materials for the solid support include, but are not limited to, gels such as agarose, gelatin, sepharose, etc., polymers such as polyacrylamide, polydimethyl acrylamide, polyethylene oxide, polyethylene glycol, hydroxy methyl cellulose, etc., plastics such as polypropylene, polymethacrylate, polystyrene, polycarbonate, polyethylene, etc., nylon, glass, silica, etc. The actual choice of material(s) will depend upon, among other factors, the desired mode of immobilization, and will be apparent to those having skill in the art.

For immobilization via adsorption or absorption, immobilized competitor oligo 10 can be conveniently prepared by contacting solid support 9 with the competitor oligo 4 for a time period sufficient for competitor oligo 4 to adsorb or absorb onto the support. Following optional wash steps, the support is then dried. The various methods described in the dot-blot or other nucleic acid blotting arts for immobilizing nucleic acids onto nitrocellulose or nylon filters can be conveniently adapted to immobilize the competitor oligo 4 onto solid support 9.

For immobilization by ionic attraction, if not inherently charged, support 9 is first activated or derivatized with charged groups prior to contacting it with competitor oligo 4, which is first modified to be oppositely charged.

For immobilization mediated by way of pairs of specific binding compounds (such as biotin-streptavidin and antibody-hapten) support 9 is first derivatized and/or coated with one member of the specific binding pair, such as streptavidin, and the derivatized support is then contacted with a competitor oligo 4 which is linked to the other member of the specific binding pair, such as biotin. Methods for derivatizing or coating a variety of materials with binding molecules such as avidin, as well as methods for linking myriad types of compounds to binding molecules such as biotin, are well known in the art. For most competitor oligos, biotin can be conveniently incorporated into the molecule at either a terminal and/or internal nucleobase, or at one or both of its carboxyl and amino termini using commercially available chemical synthesis reagents, as will be described in more detail in a later section.

In a preferred embodiment of the invention, competitor oligo 4 is covalently attached to support 9, optionally by way of one or more linking moieties. Unless the support inherently contains reactive functional groups capable of forming a covalent linkage with the competitor oligo, it must first be activated or derivatized with such reactive groups. Typical reactive groups useful for effecting covalent attachment of compounds such as competitor oligos to supports include hydroxyl, sulfonyl, amino, cyanate, isocyanate, thiocyanate, isothiocyanate, epoxy and carboxyl groups, although other reactive groups as will be apparent to those of skill in the art may also be used.

A variety of techniques for activating myriad types of solid support materials with reactive groups suitable for covalently attaching compounds thereto, including competitor oligos such as PNAs, are known in the art and include, for example, chemical activation, corona discharge activation, flame treatment activation, gas plasma activation and plasma enhanced chemical vapor deposition. Any of these techniques can be used to activate the solid support with reactive groups. For a review of the many techniques that can be used to activate or derivatize the support, see WILEY ENCYCLOPEDIA OF PACKAGING TECHNOLOGY, 2d Ed., Brody & Marsh, Ed., "Surface Treatment," pp. 867–874, John Wiley & Sons, 1997, and the references cited therein. Chemical methods suitable for generating amino groups on glass beads are described in Atkinson & Smith, "Solid Phase Synthesis of Oligodeoxyribonucleotides by the Phosphite Triester Method," In: OLIGONUCLEOTIDE SYNTHESIS: A PRACTICAL APPROACH, M J Gait, Ed., 1985, IRL Press, Oxford, particularly at pp. 45–49 (and the references cited therein); chemical methods suitable for generating hydroxyl groups on glass beads are described in Maskos et al, 1992, Nucl. Acids Res. 20(7):1679–1684 (and the references cited therein); chemical methods suitable for generating functional groups on support materials such as polystyrene, polyamides and grafted polystyrenes are described in Lloyd-Williams et al., 1997, CHEMICAL APPROACHES TO THE SYNTHESIS OF PEPTIDES AND PROTEINS, Chapter 2, CRC Press, Boca Raton, Fla. (and the references cited therein). Additional methods are well known, and will be apparent to those of skill in the art.

Competitor oligo 4 may be covalently immobilized on an activated support following synthesis and/or isolation, or, alternatively, it may be synthesized in situ directly on the support. For example, a purified PNA may be covalently immobilized on an amino-activated support, conveniently by way of its carboxy terminus. Alternatively, the PNA can be synthesized in situ directly on an amino-activated support using conventional solid-phase peptide chemistries and reagents (see WO 98/03542, U.S. Pat. No. 5,539,082, U.S. Pat. No. 5,719,262, U.S. Pat. No. 5,766,855 and U.S. Pat. No. 5,786,461 and the references cited therein).

Multiple immobilized competitor oligos having different nucleobase sequences may be conveniently synthesized in parallel using, for example, the "tea bag" approach of Houghten, 1985, Proc. Natl. Acad. Sci. USA 82: 5131–5135 (see also U.S. Pat. No. 4,631,211), the automated methods described by Zuckerman et al., 1992, Int. J. Pept. Protein Res. 40: 497–506 or the split synthesis methods described by Furka et al., 1991, Int. J. Pept. Protein Res. 37: 487–493 (see also, Sebestyen et al., 1993, Siorg. Med. Chem. Lett. 3: 413–418; Lam et al., 1991, Nature 354: 82–84 and Houghten et al., 1991, Nature 354: 84–86).

Those of skill in the art will recognize that when using in situ chemical synthesis, the covalent bond formed between the competitor oligo and the support should be substantially stable to the synthesis and deprotection conditions used so as to avoid loss of the competitor oligo during synthesis and/or deprotection. Suitable linkages are well-known and will be apparent to those of skill in the art.

Whether synthesized directly on an activated or derivatized support or immobilized on an activated or derivatized support after synthesis or isolation, the competitor oligo may be optionally spaced away from the support by way of one or more linkers. As will be appreciated by those having skill in the art, such linkers will be at least bifunctional, i.e., they will have one functional group or moiety capable of forming a linkage with the activated solid support and another functional group or moiety capable of forming a linkage with another linker molecule or the compound to be immobilized. The linkers may be long or short, flexible or rigid, hydrophobic or hydrophilic, depending on the particular application.

In certain circumstances, such linkers can be used to "convert" one functional group into another. For example, an amino-activated solid support can be converted into a carboxyl-activated support by reaction with, for example, 3-carboxy-propionic acid. In this way, solid support materials which cannot be readily activated or derivatized with a specified reactive functional group can be conveniently converted into a an appropriately activated support. Chemistries and reagents suitable for "converting" such reactive groups are well-known, and will be apparent to those having skill in the art.

Linkers can also be used, where necessary, to increase or "amplify" the number of reactive groups on the activated support. For this embodiment, the linker will typically have three or more functional groups. Following attachment to the activated support by way of one of the functional groups, the remaining two or more groups are available for attachment of the compound. Amplifying the number of functional groups on the activated support in this manner is particularly convenient when the activated support contains relatively few reactive groups.

Reagents for amplifying the number of reactive groups are well-known and will be apparent to those of skill in the art. A particularly convenient class of amplifying reagents are the multifunctional epoxides sold under the trade name DENACOL™ (Nagassi Kasei Kogyo K.K.). These epoxides contain as many as four, five, or even more epoxy groups, and can be used to amplify supports activated with reactive groups that react with epoxides, including, for example, hydroxyl, amino and sulfonyl activated supports. The resulting epoxy-activated supports can be conveniently converted to a hydroxyl-activated support, an amino-activated support, a carboxy-activated support, or other activated supports by well-known methods. Alternatively, the competitor oligo may be covalently coupled directly to the epoxide groups.

Linkers suitable for spacing biological or other molecules, including polynucleotides and competitor oligos, from solid supports are well-known in the art, and include, by way of example and not limitation, the previously-described spacer molecules, polypeptides such as polyproline or polyalanine, saturated or unsaturated bifunctional hydrocarbons such as 6-amino-caproic acid and polymers such as polyethylene glycol, etc.

In another embodiment, the capture moiety is one member of a pair of specific binding molecules, such as biotin and avidin/streptavidin or an antibody and a hapten. Biotin may be attached to the competitor oligo using any technique known in the art. For example, biotin can be attached to the competitor oligo at one or both of its termini, at another position on the backbone, or to one or more of its nucleobases. Methods for attaching biotin to competitor oligos are well known in the art, and may be accomplished using commercially available reagents, such as biotin-NHS ester, which is available from Molecular Probes, Eugene, Oreg. In this instance, the biotin-NHS ester can be covalently attached to the amino terminus of the competitor oligo, for example a PNA, using standard coupling techniques. Alternatively, the biotin may be conjugated to a PNA during synthesis using, for example, dimethoxytrityl biotin phenyl pryazolanine ester as a synthesis reagent (see, e.g., Perry O'Keefe et al., supra). Methods of synthesizing competitor oligos comprising other binding compounds, such as haptens, will be apparent to those of skill in the art.

Figure 7:
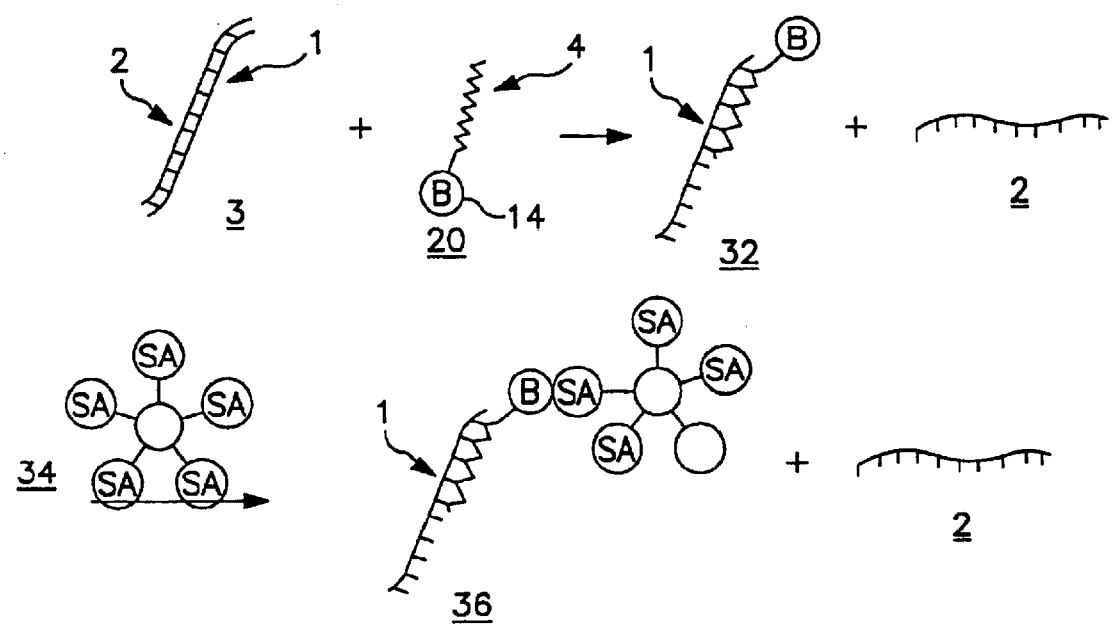
FIG. 7 illustrates an embodiment of the invention in which the competitor oligo includes a biotin capture moiety.

An embodiment of the invention employing a biotin capture moiety is illustrated in FIG. 7. Referring to FIG. 7, double-stranded target nucleic acid 3 is contacted with biotin-labeled competitor oligo 20 under conditions in which target 3 dissociates into first and second strands 1 and 2, respectively, and first strand 1 hybridizes with biotin-labeled competitor oligo 20 to yield biotin-labeled heteroduplex 32 and dissociated second strand 2. In FIG. 7, the biotin 14 is covalently attached to the terminus of competitor oligo 4. Biotin-labeled heteroduplex 32 is contacted with immobilized streptavidin, for example streptavidin-coated beads 34, under conditions conducive to binding between the biotin and streptavidin, yielding complex 36, which can be isolated and first strand 1 dissociated and isolated therefrom (see, e.g., Boffa et al., supra). Alternatively, complex 36 may be isolated and second strand 2 used without further purification.

Figure 8:
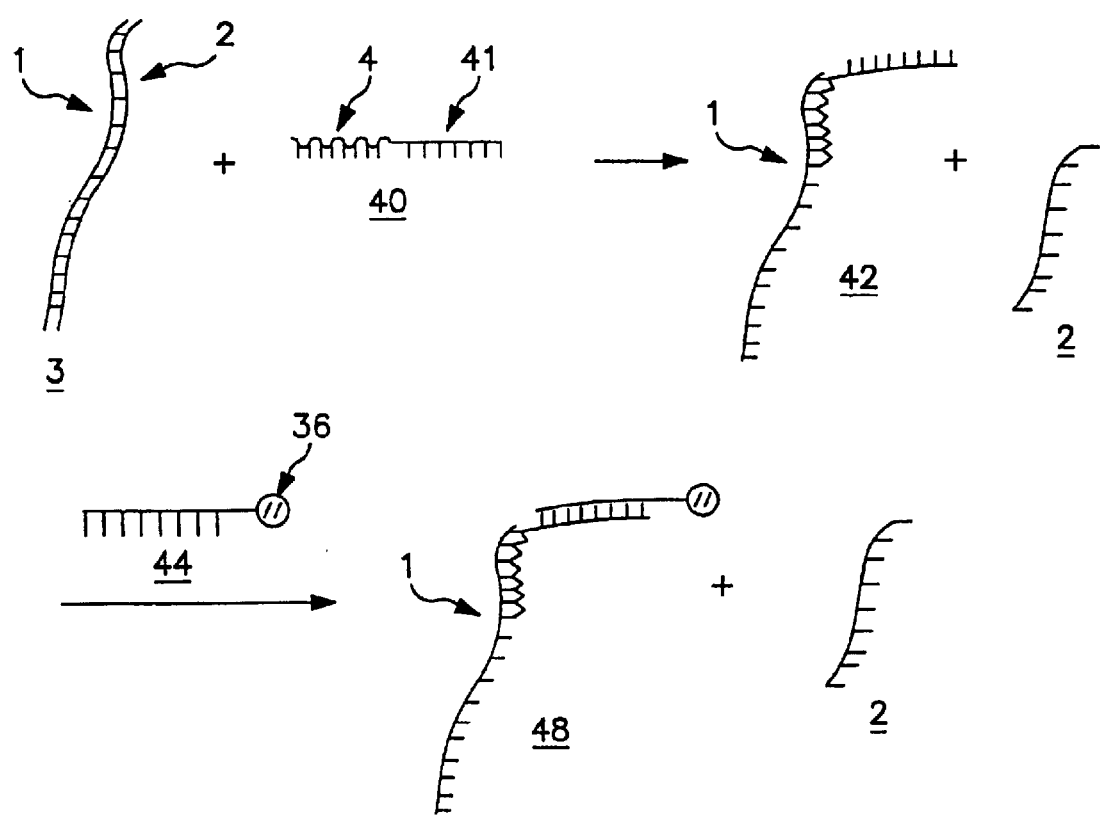
FIG. 8 illustrates an embodiment of the invention in which the competitor oligo includes a capture sequence capture moiety.

Referring to FIG. 8, in still another embodiment, the capture moiety may be a capture sequence 41. The capture sequence 41 is conjugated to competitor oligo 4 to yield probe 40. The capture sequence is complementary to capture probe 44, and is not complementary to competitor oligo 4 or either strand of the target nucleic acid 3. As illustrated in FIG. 8, double-stranded target nucleic acid 3 is contacted with probe 40 under conditions in which target 3 dissociates into first and second strands 1 and 2, respectively, and the competitor oligo portion 4 of probe 40 hybridizes with first strand 1 to yield complex 42 and dissociated second strand 2. Complex 42 is then contacted with capture probe 44 under conditions in which the capture probe 44 hybridizes to the capture sequence 41 of probe 40 to yield trimolecular complex 48. The capture probe 44 comprises an element 46 that allows the trimolecular complex 48 to be isolated. The element 46 can be any moiety known in the art for facilitating capture and/or isolation of the trimolecular complex, including, for example, the previously described capture moieties, conveniently a solid support or biotin.

Those of skill in the art will recognize that capture probe 44 should be contacted with complex 42 under conditions that favor hybridization between capture probe 44 and capture sequence 41 and that disfavor dissociation of complex 42 and reannealing or reassociation of first and second strands 1 and 2. This can be conveniently accomplished by insuring that one of capture sequence 41 and capture probe 44 is a competitor oligo and the other is an oligonucleotide having a charged or uncharged backbone. Methods for making chimeric probes 40 in which the capture sequence 41 has a charged backbone, for example an RNA or DNA oligonucleotide, are well. Preferably, capture sequence 41 has an uncharged backbone and capture probe 44 has either a charged or uncharged backbone. Most preferably, probe 40 is a PNA and capture probe 44 comprises a PNA, DNA or RNA oligonucleotide.

5.2.3 Contacting

Success of the methods of the invention lies in the ability to perform hybridizations, or to manipulate the hybridization conditions, to take advantage of the kinetic and/or thermostability differences between DNA/DNA, RNA/RNA and DNA/RNA duplexes as compared with heteroduplexes in which one strand of the heteroduplex is a competitor oligo, such as a PNA. As previously discussed, it has been discovered that the thermodynamic stabilities of PNA/DNA and PNA/RNA heteroduplexes are significantly higher over a wide range of ionic strengths than those of the corresponding DNA/DNA, DNA/RNA and RNA/RNA duplexes over a range of ionic strengths (see Egholm et al., 1993, Nature 365:566–568). Moreover, under conditions of low ionic strength, the kinetics of formation of, for example, PNA/DNA heteroduplexes is significantly faster than the kinetics of formation of DNA/DNA, DNA/RNA and RNA/RNA duplexes. The more rapid kinetics of PNA/DNA heteroduplex formation is independent of length. Thus, even in situations where, as a consequence of length, the resultant DNA/DNA, DNA/RNA or RNA/RNA duplex would be more thermostable than the resultant heteroduplex, the formation of the heteroduplex will occur more rapidly than the formation of the duplex. This difference in kinetics permits a competitor oligo to kinetically outcompete reannealing or reassociation of dissociated target strands, even in situations where the resultant reannealed target duplex is thermodynamically more stable than the kinetically favored heteroduplex. Thus, according to the methods of the invention, a combination of contact time, temperature and ionic strength is selected that favors target strand dissociation and heteroduplex formation. When these conditions are achieved, the assay solution will preferentially contain target-strand:competitor oligo heteroduplexes and dissociated target strands, permitting easy and efficient isolation of either target strand.

Those of skill in the art will appreciate that the choice of time, temperature and ionic strength will depend upon a variety of factors, including, among others, the C+G composition of the target-strand:competitor oligo heteroduplex, the length of the hybridized region of the target-strand:competitor oligo heteroduplex, the respective concentrations (and hence molar ratios) of the target nucleic acid and competitor oligo and the pH of the solution. Moreover, where it is desirable to isolate strands from a plurality of double-stranded target nucleic acids with competitor oligos that are not completely complementary to the target strand, the degree of specificity desired will affect the choice of time, temperature and ionic strength.

The relative stabilities of PNA/DNA and PNA/RNA heteroduplexes and DNA/DNA, DNA/RNA and RNA/RNA duplexes, as exemplified in the Tm, are highly dependent upon salt concentration. Generally, it has been found that PNA/DNA and PNA/RNA heteroduplexes are significantly more stable than their corresponding DNA/DNA, DNA/RNA and RNA/RNA duplexes at ionic strengths below about 50 mM NaCl. Typically, the lower the ionic strength, the greater the observed stability differences. The heteroduplex formation is also favored kinetically. For example, while relatively long DNA/DNA duplexes (e.g., >100 bps) are typically more stable than short DNA/PNA heteroduplexes (e.g., 10–20 bps) at almost any salt concentration, the former DNA/DNA duplex forms very slowly at conditions of low ionic strength. In contrast, the latter PNA/DNA heteroduplex forms very quickly. Thus, once the strands of the target nucleic acid are dissociated, under conditions of low ionic strength, heteroduplex formation between the competitor oligo and complementary target strand will kinetically out-compete reannealing or reassociation of the target strands. Accordingly, regardless of the temperature and ionic strength selected, when the resultant heteroduplex is thermodynamically less stable (as measured by $T_m$) than the reannealed or reassociated target duplex, such as when the heteroduplex is significantly shorter (e.g., ⅛ to ½) than the duplex (as measured in bp), the contact time should be short enough to prevent the hybridization from reaching equilibrium. When the thermodynamic stability of the heteroduplex (as measured by $T_m$) is approximately equal to or greater than that of the reannealed target duplex, the contact time may be long enough to permit the hybridizations to reach equilibrium. However, even in these instances it is possible to use contact times short enough to avoid reaching equilibrium, as avoiding equilibrium takes greatest advantage of the faster kinetics of heteroduplex formation, thereby permitting high efficiency recovery of the desired target strand. Generally, regardless of the lengths of the resultant heteroduplex and reannealed target duplex, contact times on the order of hours to ten hours, preferably on the order of 1–2 hours, should avoid equilibrium and therefore permit efficient recovery of a target strand.

As discussed above, for a given temperature, the stabilities of heteroduplexes are significantly higher than the stabilities of the corresponding duplexes under conditions of low ionic strength. Thus, the contacting step is preferably carried out under conditions of low, or extremely low, ionic strength. For salts having monovalent cations (e.g., NaCl and KCl), cationic strengths on the order of 10 mM or lower are preferred. For salts having divalent cations (e.g., $MgCl_2$, $ZnCl_2$, etc.), cationic strengths on the order of 1 mM or less are preferred. For trivalent salts, cationic strengths on the order of 100 $\mu$M or less are preferred.

During the contacting step, salts and other agents that are known in the art to enhance the kinetics of heteroduplex formation and/or to render the thermal melting temperature of a specified duplex less sequence-dependent (e.g., spermine, TMAC, DTAB, CTAB, TMAB, etc.) may also be used. If such agents are used, the total cationic strength of the buffer should preferably not exceed 50 mM, and more preferably it should not exceed 10 mM.

The buffer may comprise other agents commonly employed in the art of nucleic acid hybridization, such as, for example pH buffering agents, denaturing agents such as formamide, etc., and other agents. Suitable buffering agents, pH ranges and denaturing agents are described, for example, in Hames and Higgins, *Nucleic Acid Hybridization A Practical Approach*, IRL Press, Oxford, England (1989).

Typically, the contacting step is performed at a pH in the range of pH 6 to 8, and denaturing agents are not used.

As will be recognized by those of skill in the art, the temperature at which the contacting step is performed will depend, in part, on the ionic strength of the buffer. Ideally, the selected temperature will be a temperature at which the heteroduplex is thermodynamically more stable than the reannealed target duplex, although due to the kinetic differences of formation of heteroduplexes and duplexes, selection of such a temperature is not required for success. Preferably, an ionic strength will be selected that permits contacting at room temperature or between about 20° C. and about 40° C. However, other temperatures may be used, provided they produce the intended result.

The temperature may be held constant during the contacting step, or it may be cycled, typically with the aid of a thermocycler, such as the types of thermocyclers commonly employed in PCR reactions. Convenient cycling temperatures include a first temperature that is above the $T_m$ of the target nucleic acid (at the selected ionic strength) and below the $T_m$ of the target strand:competitor oligo heteroduplex and a second temperature that is above the $T_m$ of the heteroduplex. The rate at which the temperature is cycled may be rapid or slow, and is typically similar to the rates used in PCR. Alternative cycling temperatures and cycling rates that may be used will be apparent to those of skill in the art.

The ability to select an appropriate combination of time, ionic strength and temperature that permits isolation of one strand of a double-stranded target for a particular target nucleic acid and competitor oligo is within the capabilities of those having skill in the art. For example, the thermal melting temperatures ($T_m$s) of the target nucleic acid and a model heteroduplex comprising the desired competitor oligo can be obtained at a variety of different ionic strengths, and a combination of temperature and ionic strengths selected therefrom. A combination of temperature and ionic strength may be selected that maximizes the difference in stability between the target nucleic acid and the model heteroduplex, i.e., a temperature and ionic strength at which the difference between the respective $T_m$s of the model heteroduplex and target nucleic acid is greatest. Alternatively, if a specified temperature is desired (for example room temp.), an appropriate ionic strength may be selected. Once a specified temperature and ionic strength are selected, an optimal contact time may be determined empirically.

The model heteroduplex can be manipulated to ideally represent the desired strand separation assay and/or target nucleic acid. For example, if the strand to be isolated is a DNA, the model heteroduplex may be a DNA oligo:competitor oligo heteroduplex. The DNA oligo can be the same length as the competitor oligo or longer or shorter, depending on the particular system. The sequence composition of the model heteroduplex can be manipulated to represent the degree of complementarity desired for the particular strand separation assay.

The methods of the invention are to be distinguished from methods in which a double-stranded target nucleic acid is hybridized with a complementary oligonucleotide or oligonucleotide analog to form a D-loop or other structure comprising the first and second strands of the target and the oligo. By virtue of manipulating the parameter of the assay, including, for example, the length of the competitor oligo and the ionic strength, temperature and contact time of the assay, heteroduplexes between the competitor oligo and the strand of the target are formed that are free of the other strand of the target. However, those of skill in the art will recognize complete dissociation of all of the molecules of the target strand is not necessary to achieve a useful result. All that is required is that a fraction of the target molecules present in the sample completely dissociate such that bimolecular target-strand:competitor oligo heteroduplexes are formed. Once formed, the heteroduplexes and/or dissociated target strands are captured prior to re-annealing of the target strands. Thus, as used herein, the expression, "dissociation of the target" and other equivalent expressions are intended to refer to a degree of target dissociation that provides a useful result.

Owing in part to the ability of competitor oligos such as PNAs to invade double-stranded nucleic acids, the concentration of competitor oligo can be used as a means of driving the efficiency of the dissociation. While not intending to be bound by any particular theory of operation, an invading competitor oligo will destabilize the target nucleic acid, aiding its dissociation. Since the invading reaction is a multimolecular process, it is concentration dependent. However, the actual concentrations of target nucleic acid and competitor oligo used are not critical for success, and concentrations that range from as low as pM or lower to mM or higher for either the target nucleic acid and/or competitor oligo may be used. Of greater importance is the competitor oligo:target nucleic acid molar ratio. Since the formation of a competitor:target D-loop is a bimolecular process, using competitor oligo:target nucleic acid molar ratios that are greater than 1 may help drive the efficiency of the target dissociation and heteroduplex formation achieved. Typically, competitor oligo:target molar concentration ratios in the range of 1:1 to 50:1 are used, with ratios in the range of 1:1 to 10:1 being preferred.

Figure 4:
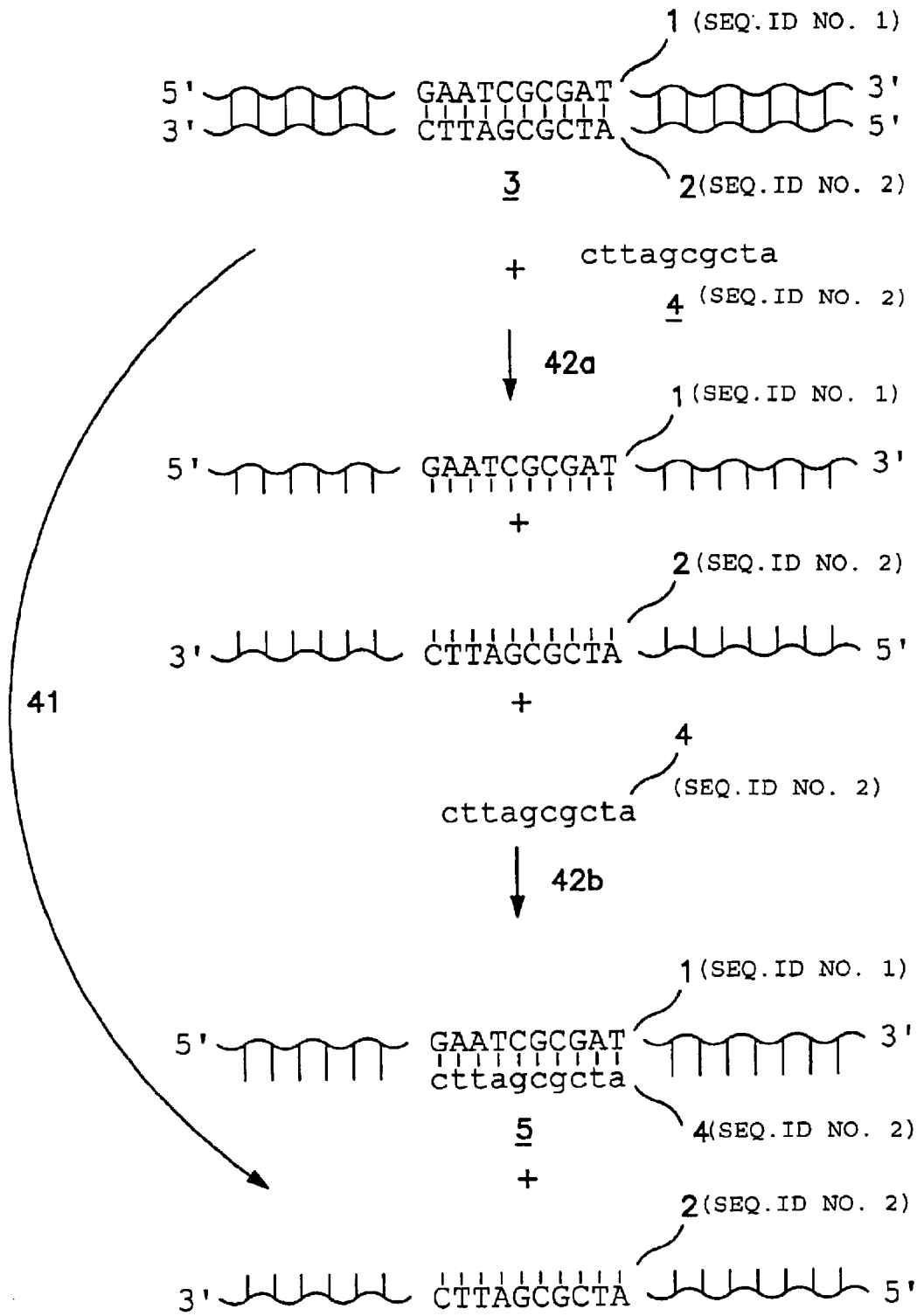
FIG. 4 illustrates embodiments of the invention in which the contacting step is performed simultaneously with, or prior to, the dissociation step.

Target strands may be isolated from a double-stranded target nucleic acid according to the invention in a variety of different embodiments. Referring to FIG. 4, the double-stranded target nucleic acid 3 can be contacted with the competitor oligo 4 without first dissociating the target 3 into first and second strands 1 and 2. In one embodiment, the contact conditions used are those in which the double-stranded target 3 is stable (i.e., tends not to dissociate). For example, target 3 may be contacted with competitor oligo 4 under conditions of physiological pH, temperature and ionic strength. In one version of this embodiment, the conditions are then altered, for example by dialysis to lower the ionic strength, to conditions which simultaneously favor dissociation of the double-stranded target nucleic acid 3 into first and second strands 1 and 2 and hybridization of the competitor oligo 4 to the first strand 1, as previously described. These altered conditions are illustrated in FIG. 4 as Δ1. Methods of selecting such conditions are described, supra.

In another version of this embodiment, the conditions are first changed to conditions that promote or favor dissociation of the target nucleic acid, but do not favor hybridization of the competitor oligo 4 to the first strand 1 (illustrated in FIG. 4 as Δ2a). Exemplary conditions Δ2a include, for example, a temperature that is above the $T_m$ of the heteroduplex 5. Hybridization of the competitor oligo 4 to the first strand 1 is then achieved by further altering the conditions to those that favor target dissociation and first-strand:competitor oligo heteroduplex 5 formation, as previously described (illustrated in FIG. 4 as Δ2b).

Figure 5:
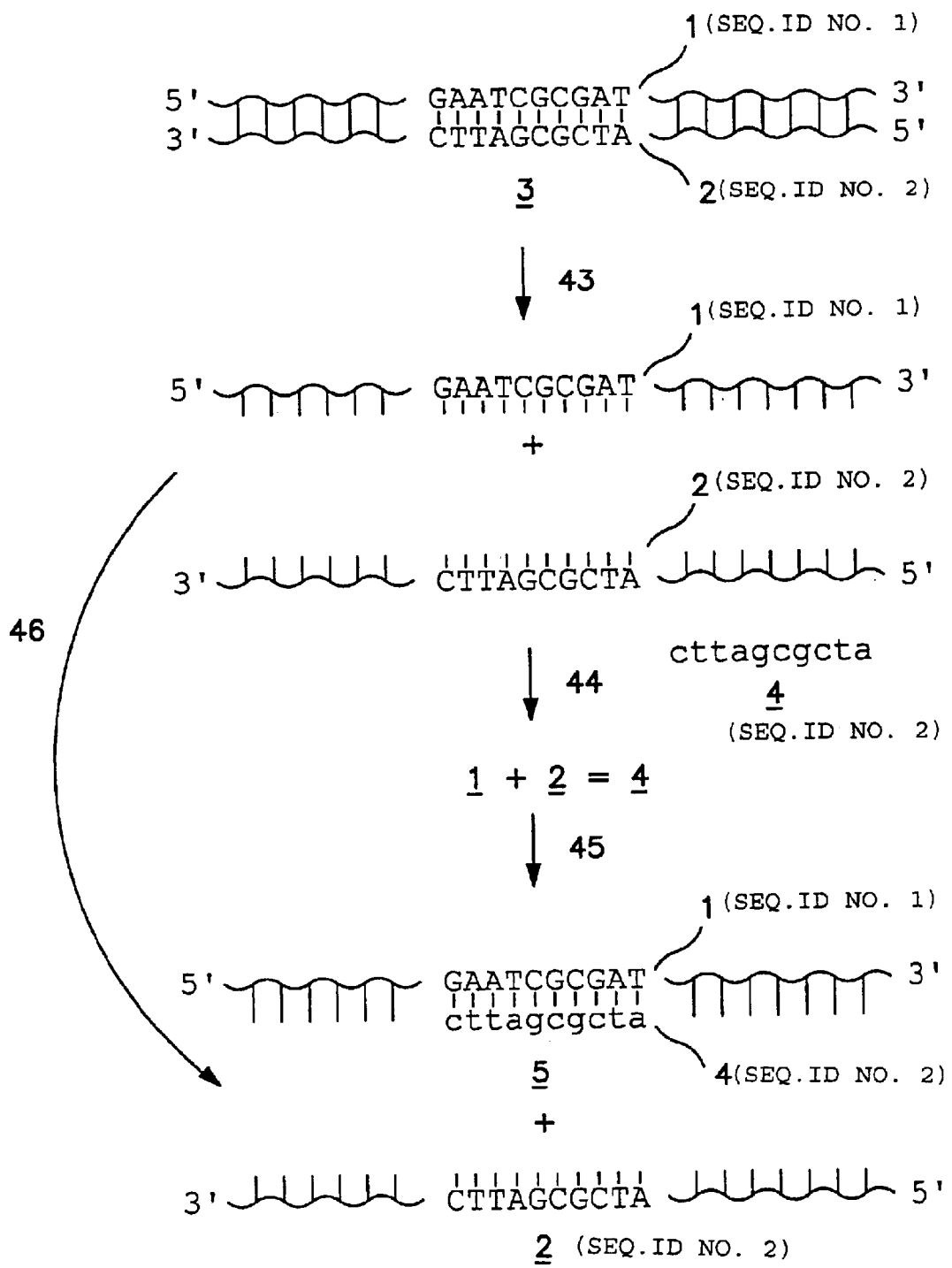
FIG. 5 illustrates embodiments of the invention in which the contacting step follows the dissociation step.

Referring to FIG. 5, in another embodiment, the double-stranded target nucleic acid is first dissociated, or denatured, into first and second strands 1 and 2, respectively prior to contact with the competitor oligo 4. In one version of this embodiment, the denaturing conditions are conditions which simultaneously promote first strand:competitor oligo heteroduplex 5 formation (illustrated by Δ3). In this embodiment, the conditions do not require further adjustment after contact with competitor oligo 4. In another version of this embodiment, the denaturing conditions do not promote first strand:competitor oligo heteroduplex formation (illustrated by Δ4). For example, target nucleic acid 3 can be denatured by boiling followed by rapid cooling with, for example, an ice bath or by other conventional means. In this embodiment, the denaturing conditions are then altered after the contacting step in order to promote first strand:competitor oligo 5 heteroduplex formation (illustrated by Δ5). Conditions useful for performing the method according to these alternative embodiments are described above. Adapting the conditions for use with the embodiments illustrated in FIG. 5 is within the capabilities of those having skill in the art. Referring to FIG. 1, regardless of the mode, following dissociation of the double-stranded target 3 and formation of first strand:competitor oligo heteroduplex 5, one strand of the target may be isolated. Either the unhybridized dissociated second strand 2 or the first strand:competitor oligo heteroduplex 5 may be recovered. If the heteroduplex 5 is recovered, it may be dissociated and the first strand 1 isolated therefrom.

Second strand 2 and heteroduplex 5 may be isolated from one another using virtually any standard technique. For example, the dissociated second strand 2 and heteroduplex 5 can be separated from one another using gel electrophoresis (see Perry-O'Keefe et al., 1996, Proc. Natl. Acad. Sci. USA 93:14670–14675). Under non-denaturing conditions, the second strand 2 and heteroduplex 5 each migrate as a discrete group which can be detected using standard techniques (e.g., using ethidium bromide). Typically, heteroduplex 5 will migrate more slowly through the gel matrix than the dissociated strand 2. Either group of molecules can be isolated from the other by excision of the respective band and elution from the gel using techniques well known in the art (see, e.g., Sambrook et al., supra).

Preferably, the competitor oligo is conjugated with, or modified to include, a capture moiety, such as a solid support, a binding molecule such as biotin or a capture sequence, as previously described (see, e.g., FIGS. 6–8). In this instance, capture of the first-strand:competitor oligo heteroduplex 5 is achieved utilizing the capture moiety. The capture conditions will depend upon the nature of the capture moiety and will be apparent to those having skill in the art. The first strand may be dissociated and isolated from the heteroduplex or, alternatively, the dissociated second strand may be recovered and used without further purification, as previously described.

5.2.4 Detection of Hybridization

Following capture and optional washing, the presence or absence of hybridization between the first strand and the competitor oligo may be optionally determined. The mode of detection will depend on whether the first strand bears a reporter molecule, and if so, the type of reporter molecule. For example, if the first strand bears a radioisotope label, the captured complex may be detected for radioactivity; if the first strand bears a fluorophore label, the captured complex may be analyzed for fluorescence; if the first strand bears a biotin label, the captured complex may be assayed for the ability to bind labeled (e.g., fluorescently labeled) avidin or streptavidin. Those of skill in the art will recognize that virtually any reporter group and detection scheme may be easily adapted for use with the present invention. In many instances, the quantity of reporter group may be determined, thereby determining the quantity of first strand isolated from the sample.

5.2.5 Uses

The methods of the invention may be used in virtually any application where the isolation of one strand of a double-stranded target nucleic acid is desirable. Due to their ability to provide easy and efficient recovery, the methods described herein may be advantageously used to purify a first strand from a double-stranded target nucleic acid that is a PCR amplification product from a pool of related or unrelated sequences in high yield for subsequent use.

The methods of the invention also permit capture and/or recovery of the first strand of a double-stranded target nucleic acid from biological samples or other samples containing large molecule contaminants. Once captured, the first strand may be used directly for PCR, sequencing, or other applications. Alternatively, the second strand may be purified and used in subsequent applications.

Thus, as will be appreciated by those of skill in the art, target nucleic acids isolated by the methods of the invention may be used advantageously in any application requiring single-stranded nucleic acid, such as, for example, the detection of single nucleotide polyphorphisms, Sanger-type or other nucleic acid sequencing methods, etc.

Various embodiments of the invention have been described. The descriptions are intended to be illustrative of the invention and not limiting. Indeed, it will be apparent to those of sill in the art that modifications may be made to the various embodiments of the invention described without departing from the spirit of the invention or scope of the appended claims set forth below.

We claim:

1. A method of isolating one strand of a double-stranded target nucleic acid, comprising: (i) contacting a double-stranded target nucleic acid comprising a first strand and a second strand with a competitor oligo capable of hybridizing to the first strand under conditions in which the first strand dissociates from the second strand and hybridizes with the competitor oligo to form a first-strand:competitor oligo heteroduplex; and (ii) isolating the dissociated second strand.

2. A method of isolating one strand of a double-stranded target nucleic acid, comprising: (i) contacting a double-stranded target nucleic acid comprising a first strand and a second strand with a competitor oligo capable of hybridizing to the first strand under conditions in which the first strand dissociates from the second strand and hybridizes with the competitor oligo to form a first-strand:competitor oligo heteroduplex; (ii) isolating the heteroduplex, and (iii) dissociating the heteroduplex and isolating the first strand.

3. A method of isolating one strand of a double-stranded target nucleic acid, comprising: (i) dissociating the double-stranded target nucleic acid into a first strand and a second strand; (ii) contacting the dissociated target nucleic acid with a competitor oligo capable of hybridizing to the first strand under conditions which favor first-strand:competitor oligo heteroduplex formation and disfavor reannealing of the first and second strands; and (iii) isolating the dissociated second strand.

4. A method of isolating one strand of a double-stranded target nucleic acid, comprising: (i) dissociating the double-stranded target nucleic acid into a first strand and a second strand; (ii) contacting the dissociated target nucleic acid with a competitor oligo capable of hybridizing to the first strand under conditions which favor first-strand:competitor oligo heteroduplex formation and disfavor reannealing of the first and second strands; (iii) isolating the heteroduplex, and (iv) dissociating the heteroduplex and isolating the first strand.

5. The method of claim 1 or 2 or 3 or 4 in which the double-stranded target nucleic acid is a double-stranded DNA.

6. The method of claim 1 or 2 or 3 or 4 in which the double-stranded target nucleic acid is a double-stranded DNA/RNA hybrid duplex.

7. The method of claim 1 or 2 or 3 or 4 in which the competitor oligo is composed of between 7 and 40 nucleobases.

8. The method of claim 1 or 2 or 3 or 4 in which the double-stranded target nucleic acid has the formula:

TAIL 1-SEQUENCE-TAIL 2 TAIL 1'-SEQUENCE'-TAIL 2' wherein: TAIL 1 represents a first tail nucleobase sequence; SEQUENCE represents a target nucleobase sequence; TAIL 2 represents a second tail nucleobase sequence; TAIL 1' represents a nucleobase sequence that is complementary to TAIL 1; SEQUENCE' represents a nucleobase sequence that is complementary to SEQUENCE; and TAIL 2' represents a nucleobase sequence that is complementary to TAIL 2.

9. The method of claim 8 in which a portion of the competitor oligo is capable of hybridizing to TAIL 1 and another portion of the competitor oligo is capable of hybridizing to TAIL 2.

10. The method of claim 8 in which a portion of the competitor oligo is capable of hybridizing to TAIL 1' and another portion of the competitor oligo is capable of hybridizing to TAIL 2'.

11. The method of claim 8 in which TAIL 1 and TAIL 2 comprise non-standard synthetic nucleobases.

12. The method of claim 8 in which TAIL 1 and TAIL 2 are not complementary to one another.

13. The method of claim 1 or 2 or 3 or 4, in which the competitor oligo includes a capture moiety.

14. A The method of claim 13, in which the capture moiety is one member of a pair of molecules that specifically bind to each other.

15. The method of claim 13, in which the capture moiety is biotin.

16. The method of 13, in which the capture moiety is a solid support.

17. The method of claim 16, in which the solid support is magnetic.

18. The method of claim 13 in which the capture moiety is a capture sequence.

19. The method of claim 13 in which the capture moiety is a charged group.

20. The method of claim 1 or 2 or 3 or 4 in which the competitor oligo is capable of hybridizing to only the first or the second strand of the double-stranded target nucleic acid.

21. The method of claim 1 or 2 or 3 or 4 in which the contacting step is carried out at a cationic strength in the range of 0 to 10 mM, a pH in the range of 6 to 8, and a temperature in the range of 20 to 40° C.

22. The method of claim 1 or 2 or 3 or 4 in which the competitor oligo is a PNA and optionally includes from 1 to 4 positively charged nucleobase interlinkages.

23. The method of claim 1 or 2 or 3 or 4 in which the competitor oligo comprises nonstandard synthetic nucleobases.

24. A method of isolating one strand of a double-stranded target nucleic acid, comprising the steps of: (i) dissociating the double-stranded target nucleic acid into a first strand and a second strand; (ii) contacting the dissociated target nucleic acid with a competitor oligo capable of hybridizing to only the first strand under conditions which kinetically favor competitor oligo first-strand hybrid formation and kinetically disfavor reannealing of the first and second strands, said competitor oligo being conjugated with a moiety that facilitates capture of competitor oligo:first-strand hybrids; (iii) capturing the competitor oligo:first strand hybrid, and (iv) dissociating the heteroduplex and isolating the first strand.

25. The method of claim 24 wherein the competitor oligo is a PNA.

* * * * *

UNITED STATES PATENT AND TRADEMARK OFFICE
CERTIFICATE OF CORRECTION

PATENT NO.        : 6,787,310 B2
APPLICATION NO.   : 09/909001
DATED             : September 7, 2004
INVENTOR(S)       : Chiesa et al.

It is certified that error appears in the above-identified patent and that said Letters Patent is hereby corrected as shown below:

In column 32, line 28, please re-number claim 5 as claim number 3;
In column 32, line 28, please delete "3 or 4" and insert --24 or 25--;

In column 32, line 57, please re-number claim 6 as claim number 4;
In column 32, line 57, please delete "3 or 4" and insert --24 or 25--;

In column 32, line 60, please re-number claim 7 as claim number 5;
In column 32, line 60, please delete "3 or 4" and insert --24 or 25--;

In column 32, line 63, please re-number claim 8 as claim number 6;
In column 32, line 63, please delete "3 or 4" and insert --24 or 25--;

In column 33, line 8, please re-number claim 9 as claim number 7;
In column 33, line 8, please delete "8" and insert --6--;

In column 33, line 12, please re-number claim 10 as claim number 8;
In column 33, line 12, please delete "8" and insert --6--;

In column 33, line 16, please re-number claim 11 as claim number 9;
In column 33, line 16, please delete "8" and insert --6--;

In column 33, line 18, please re-number claim 12 as claim number 10;
In column 33, line 18, please delete "8" and insert --6--;

In column 33, line 20, please re-number claim 13 as claim number 11;
In column 33, line 20, please delete "3 or 4" and insert --24 or 25--;

In column 33, line 22, please re-number claim 14 as claim number 12;
In column 33, line 22, please delete "13" and insert --11--;

In column 33, line 25, please re-number claim 15 as claim number 13;
In column 33, line 25, please delete "13" and insert --11--;

In column 33, line 27, please re-number claim 16 as claim number 14;
In column 33, line 27, please delete "13" and insert --11--;

UNITED STATES PATENT AND TRADEMARK OFFICE
CERTIFICATE OF CORRECTION

PATENT NO.         : 6,787,310 B2
APPLICATION NO.  : 09/909001
DATED                  : September 7, 2004
INVENTOR(S)       : Chiesa et al.

It is certified that error appears in the above-identified patent and that said Letters Patent is hereby corrected as shown below:

In column 33, line 29, please re-number claim 17 as claim number 15;
In column 33, line 29, please delete "16" and insert --14--;

In column 33, line 31, please re-number claim 18 as claim number 16;
In column 33, line 31, please delete "13" and insert --11--;

In column 34, line 1, please re-number claim 19 as claim number 17;
In column 34, line 1, please delete "13" and insert --11--;

In column 34, line 3, please re-number claim 20 as claim number 18;
In column 34, line 3, please delete "3 or 4" and insert --24 or 25--;

In column 34, line 6, please re-number claim 21 as claim number 19;
In column 34, line 6, please delete "3 or 4" and insert --24 or 25--;

In column 34, line 10, please re-number claim 22 as claim number 20;
In column 34, line 10, please delete "3 or 4" and insert --24 or 25--;

In column 34, line 13, please re-number claim 23 as claim number 21;
In column 34, line 13, please delete "3 or 4" and insert --24 or 25--;

In column 34, line 16, please re-number claim 24 as claim number 22;

In column 34, line 29, please re-number claim 25 as claim number 23;
In column 34, line 29, please delete "24" and insert --22--;

UNITED STATES PATENT AND TRADEMARK OFFICE
CERTIFICATE OF CORRECTION

PATENT NO. : 6,787,310 B2
APPLICATION NO. : 09/909001
DATED : September 7, 2004
INVENTOR(S) : Chiesa et al.

It is certified that error appears in the above-identified patent and that said Letters Patent is hereby corrected as shown below:

Col. 35 lines 16-28
    Please insert claim number 24:

24.    A method of isolating one strand of a double-stranded target nucleic acid, comprising: (i) dissociating the double-stranded target nucleic acid into a first strand and a second strand; (ii) contacting the dissociated target nucleic acid with a competitor oligo capable of hybridizing to the first strand under conditions which favor first-strand:competitor oligo heteroduplex formation and disfavor reannealing of the first and second strands; and (iii) isolating the dissociated second strand.

Col. 35 lines 29-34
    Please insert claim number 25:

25.    A method of isolating one strand of a double-stranded target nucleic acid, comprising: (i) dissociating the double-stranded target nucleic acid into a first strand and a second strand; (ii) contacting the dissociated target nucleic acid with a competitor oligo capable of hybridizing to the first strand under conditions which favor first-strand:competitor oligo heteroduplex formation and disfavor reannealing of the first and second strands; (iii) isolating the heteroduplex, and (iv) dissociating the heteroduplex and isolating the first strand.

Signed and Sealed this

Seventh Day of October, 2008

JON W. DUDAS
*Director of the United States Patent and Trademark Office*